US011052129B2

(12) United States Patent
Weston-Davies

(10) Patent No.: US 11,052,129 B2
(45) Date of Patent: Jul. 6, 2021

(54) ORNITHODOROS MOUBATA COMPLEMENT INHIBITOR FOR USE IN THE TREATMENT OF COMPLEMENT-MEDIATED DISEASES IN PATIENTS WITH C5 POLYMORPHISM

(71) Applicant: Volution Immuno Pharmaceuticals SA, Geneva (CH)

(72) Inventor: Wynne H. Weston-Davies, Salperton (GB)

(73) Assignee: Volution Immuno Pharmaceuticals SA, Geneva (CH)

( * ) Notice: Subject to any disclaimer, the term of this patent is extended or adjusted under 35 U.S.C. 154(b) by 466 days.

(21) Appl. No.: 15/315,136

(22) PCT Filed: Jun. 8, 2015

(86) PCT No.: PCT/EP2015/062742
§ 371 (c)(1),
(2) Date: Nov. 30, 2016

(87) PCT Pub. No.: WO2015/185760
PCT Pub. Date: Dec. 10, 2015

(65) Prior Publication Data
US 2017/0196936 A1    Jul. 13, 2017

(30) Foreign Application Priority Data
Jun. 6, 2014  (GB) ...................................... 1410116

(51) Int. Cl.
*A61K 38/17* (2006.01)
*A61P 37/00* (2006.01)
(52) U.S. Cl.
CPC .......... *A61K 38/1767* (2013.01); *A61K 38/17* (2013.01); *A61P 37/00* (2018.01)
(58) Field of Classification Search
CPC ............................ A61K 38/1767; A61P 37/00
See application file for complete search history.

(56) References Cited

U.S. PATENT DOCUMENTS

| 9,192,648 B2 | 11/2015 | Hamer et al. |
| 2005/0054033 A9 | 3/2005 | Moore et al. |
| 2012/0283167 A1 | 11/2012 | Weston-Davies |
| 2018/0193417 A1 | 7/2018 | Weston-Davies |

FOREIGN PATENT DOCUMENTS

| JP | 2012516694 A | 7/2012 |
| WO | 2004106369 A2 | 12/2004 |
| WO | 2007028968 A1 | 3/2007 |
| WO | 2008029167 A1 | 3/2008 |
| WO | 2008029169 A2 | 3/2008 |
| WO | 2009098454 A2 | 8/2009 |
| WO | 2010100396 A1 | 9/2010 |
| WO | 2011083317 A1 | 7/2011 |
| WO | 2014047500 A1 | 3/2014 |
| WO | 2018193122 A1 | 10/2018 |

OTHER PUBLICATIONS

Nishimura, et al. (Genetic Variants in C5 and Poor Response to Eculizumab, The New England Journal of Medicine 2014, 370:632-639) (Year: 2014).*
Delves (Complement System, Merck Manual 2017) (Year: 2017).*
Nunn, et al. (Complement Inhibitor of C5 Activation from the Soft Tick *Ornithodoros moubata*, The Journal of Immunology 2005, 174:2084-2091 (Year: 2005).*
Nishimura, et al. (Genetic Variants in C5 and Poor Response to Eculizumab, NEJM 2014, 370:632-639, of record) (Year: 2014).*
Nunn, et al. (Complement Inhibitor of C5 Activation from the Soft Tick *Ornithodoros moubata*, The Journal of Immunology 2005, 174:2084-2091, of record). (Year: 2005).*
Shobha et al., "An exploratory survey to identify the adolescents with high risk for Polycystic Ovarian Syndrome (PCOS) and to find the effectiveness of an awareness programme among students of selected pre university colleges of Udupi District", IOSR Journal of Nursing and Health Science, 2014, 66-69 (Year: 2014).*
Mayo Clinic, Prostate Cancer, pp. 1-4, obtained https://www.mayoclinic.org/diseasesconditions/prostate-cancer/symptoms-causes/syc-20353087?p=1 on Mar. 30, 2020 (Year: 2020).*
Weston-Davies et al., "Clinical and Immunological Characterisation of Coversin, a Novel Small Protein Inhibitor of Complement C5 with Potential As a Therapeutic Agent in PNH and Other Complement Mediated Disorders," 56th ASH Annual Meeting and Exposition, pp. 1-2, Dec. 17, 2014.
Mastellos et al., "Complement in paroxysmal nocturnal hemoglobinuria: exploiting our current knowledge to improve the treatment landscape—Author Manuscript", Expert Review of Hematology, Apr. 2, 2015 (Apr. 2, 2015), pp. 1-26.
Jun-Ichi Nishimura et al., "Genetic Variants in C5 and Poor Response to Eculizumab", New England Journal of Medicine, vol. 370, No. 7, pp. 632-639, Feb. 13, 2014.

(Continued)

*Primary Examiner* — Lianko G Garyu

(74) *Attorney, Agent, or Firm* — McNeill Baur PLLC

(57) ABSTRACT

The present invention relates to methods of treating or preventing a complement-mediated disease and/or disorder in a subject with a complement C5 polymorphism, including administering to a subject in need thereof a therapeutically or prophylactically effective amount of an agent that a) inhibits the classical complement pathway, the alternative complement pathway and the lectin complement pathway; and/or b) inhibits eicosanoid activity. The invention also relates to methods of identifying patient populations with C5 polymorphisms that are treatable with specific agents that a) inhibit the classical complement pathway, the alternative complement pathway and the lectin complement pathway; and/or b) inhibit eicosanoid activity.

30 Claims, 8 Drawing Sheets
Specification includes a Sequence Listing.

(56) References Cited

OTHER PUBLICATIONS

Chandrasekhar: "Complement C5", UCSD Molecule Pages, vol. I, No. 2, p. 62, Jan. 1, 2012.
Orth-Holler et al., "Inhibition of terminal complement activation in severe Shiga toxin-associated HUS—perfect example for a fast track from bench to bedside", EMBO Molecular Medicine, vol. 3, No. 11, pp. 617-619, Nov. 23, 2011.
Hepburn et al., "In vivo characterization and therapeutic efficacy of a C5-specific inhibitor from the soft tick Ornithodoros moubata", Journal of Biological Chemistry, American Society for Biochemistry and Molecular Biology, US, vol. 282, No. 11, pp. 8292-8299, Mar. 16, 2007.
Soltys et al., "Novel complement inhibitor limits severity of experimentally myasthenia gravis", Annals of Neurology, vol. 65, No. I, pp. 67-75, Jan. 4, 2009.
Barratt-Due et al., "Omithodoros moubata Complement Inhibitor Is an Equally Effective C5 Inhibitor in Pigs and Humans" and , The Journal of Immunology, vol. 187, No. 9, pp. 4913-4919, Nov. 1, 2011.
Carrera-Marin et al., "C5 Inhibitor rEV576 Ameliorates in Vivo Effects of Antiphospholipid Antibodies," ACR Meeting, Arthritis & Rheumatism, vol. 63, No. SIO, p. S5, Oct. 2011.
Fredslund et al., "Structure of and influence of a tick complement inhibitor on human complement component 5" , Nature Immunology, Nature Publishing Group, vol. 9, No. 7, Jul. 2008, pp. 753-760.
Roversi et al., "The Structure of OMCI, a Novel Lipocalin Inhibitor of the Complement System," Journal of Molecular Biology, 369(3-3):784, May 11, 2007, 17 pages.
Zuber et al., "Use of eculizumab for atypical haemolytic uraemic syndrome and C3 glomerulopathies," Nature Reviews Nephrology, vol. 8, No. 11, Oct. 2, 2012 (Oct. 2, 2012), pp. 643-657.
Written Opinion of the International Searching Authority in International Application No. PCT/EP2015/062742, dated Oct. 12, 2015 (35 pages).
International Search Report in International Application No. PCT/EP2015/062742, dated Oct. 12, 2015 (8 pages).
Anonymous, "7th International Conference on Complement Therapeutics—Aegean Conferences," Jun. 6, 2014 (12 Pages).
Weston-Davies et al., "Coversin is a promising new clinical anti-complement agent," presentation at World Complement Therapeutics meeting, Rio de Janeiro, Sep. 2014 (19 slides).
Brodsky et al., "Eculizumab: another breakthrough," Blood, vol. 129, No. 8, Feb. 2017, pp. 922-923.
De Latour et al., "Assessing complement blockade in patients with paroxysmal nocturnal hemoglobinuria receiving eculizumab," Blood, vol. 125, No. 5, Jan. 29, 2015, pp. 775-783.
Delgado-Cervino et al., "C5 complement deficiency in a Spanish family Molecular characterization of the double mutation responsible for the defect," Molecular Immunology 42 (2005) pp. 105-111.
Goodship et al., "Use of the complement inhibitor Coversin to treat HSCT-associated TMA," Blood Advances, vol. 1, No. 16, pp. 1254-1258, Jul. 11, 2017.
Guo et al.,"Role of C5A in Inflammatory Responses," Annu. Rev. Immunol. 2005. 23:821-52.
Halangk et al., "Evaluation of complement factor 5 variants as genetic risk factors for the development of advanced fibrosis in chronic hepatitis C infection, " Journal of Hepatology 49 (2008) 339-345.
Harder et al., "Incomplete inhibition by eculizumab: mechanistic evidence for residual C5 activity during strong complement activation," Blood, vol. 129, No. 8, pp. 970-980, Feb. 23, 2017.
He et al., "Complement Inhibitors Targeted to the Proximal Tubule Prevent Injury in Experimental Nephrotic Syndrome and Demonstrate a Key Role for C5b-9," J Immunol 2005; 174:5750-5757.
Hobart et al., "Polymorphism of human C5," Ann. Hum. Genet. (1981), 45, 1-4.
Jaskowski et al., "Comparison of Three Different Methods for Measuring Classical Pathway Complement Activity," Clin. Diagn. Lab. Immunol., vol. 6, No. 1, p. 137-139, Jan. 1999.
Jore et al., "Structural basis for therapeutic inhibition of complement C5," Nat Struct Mol Biol. May 2016;23(5):378-86.
Jore et al., Supplementary Figures, "Structural basis for therapeutic inhibition of complement C5," Nat Struct Mol Biol. May 2016 (15 pages) (doi:10.1038/nsmb.3196).
Mead et al., "The Membrande Attack Complex of Complement Causes Severe Demyelination Associated with Acute Axonal Injury," J Immunol 2002; 168:458-465.
Nakashima et al., "Membrane Attack Complex Contributes to Destruction of Vascular Integrity in Acute Lung Allograft Rejection," J Immunol 2002; 169:4620-4627.
Neumann et al., "Local Production of Complement Proteins in Rheumatoid Arthritis Synovium," Arthritis and Rheumatism, vol. 46, No. 4, Apr. 2002, pp. 934-945.
Papagianni et al., "C5b-9 and adhesion molecules in human idiopathic membranous nephropathy," Nephorl Dial Transplant 17: 57-63 (2002).
Pfarr et al., "Linking C5 Deficiency to an Exonic Splicing Enhancer Mutation," J Immunol 2005; 174:4172-4177.
Pfarr et al., "Linking C5 Deficiency to an Exonic Splicing Enhancer Mutation" (Erratum), J Immunol 2009; 182:5152.
Pischke et al., "Complement factor 5 blockade reduces porcine myocardial infarction size and improves immediate cardiac function," Basic Res Cardiol (2017) 112:20, 14 pages.
Quigg et al., "Complement and Autoimmune Glomerular Diseases," Curr Dir Autoimmun., vol. 7, pp. 165-180 (2004).
Ricklin et al., "Complement-targeted therapeutics," Nature Biotechnology, vol. 25, No. 11, pp. 1265-1275 (Nov. 2007).
Ricklin et al., "New milestones ahead in complement-targeted therapy," Seminars in Immunology 28 (2016) 208-222.
Sahu et al., "Complement inhibitors: a resurgent concept in anti-inflammatory therapeutics," Immunopharmacology 49 (2000) 133-148.
Schatz-Jakobsen et al., "Structural Basis for Eculizumab-Mediated Inhibition of the Complement Terminal Pathway," J Immunol 197:337-344; May 18, 2016.
Skejflo et al. "Combined inhibition of complement and CD14 improved outcome in porcine polymicrobial sepsis," Critical Care (2015) 19:415, 8 pages.
Terpe et al., "Overview of tag protein fusions: from molecular and biochemical fundamentals to commercial systems," Appl Microbiol Biotechnol (2003) 60:523-533.
Volk et al., "Stratification of responders towards eculizumab using a structural epitope mapping strategy," Sci. Rep. 6, 31365; doi: 10.1038/srep31365 (2016).
Wang et al., "Inherited Human Complement C5 Deficiency," The Journal of Immunology, 1995, 154:5464-5471.
Williams et al., "Deletion of the Gene Encoding CD59a in Mice Increases Disease Severity in a Murine Model of Rheumatoid Arthritis," Arthritis and Rheumatism, vol. 50, No. 9, Sep. 2004, pp. 3035-3044.
Huber-Lang et al., "Double Blockade of CD14 and Complement C5 Abolishes the Cytokine Storm and Improves Morbidity and Survival in Polymicrobial Sepsis in Mice," J Immunol Apr. 30, 2014, 1400341; DOI: https://doi.org/10.4049/jimmunol.1400341 (10 pages including supplementary information; republished at vol. 192, pp. 5324-5331).
Weston-Davies, "Phase 1 Clinical trial of complement C5 inhibitor coversin," Molecular Immunology, 2013, vol. 56, Issue 3, p. 264 CDT3.
Halstead et al., "C5 inhibitor rEV576 protects against neural injury in an in vitro mouse model of Miller Fisher syndrome," Journal of the Peripheral Nervous System 13:228-235 (2008).
Cravedi et al., "Complement Regulation of T-Cell Alloimmunity. Semin Nephrol," 33(6): pp. 1-18 (2013).
Guo et al., "Role of C5A in Inflammatory Responses," Annu. Rev. Immunol, 23:821-52 (2005).
Jodele et al., Eculizumab Therapy in Children with Severe Hematopoietic Stem Cell Transplant-Associated Thrombotic Microangiopathy, Biol. Blood Marrow Transplant, 2014, vol. 20(4), pp. 518-525.
Martin et. al., "First-and second-line systemic treatment of acute graft-versus-host disease: recommendations of the American Soci-

(56) References Cited

OTHER PUBLICATIONS ety of Blood and Marrow Transplantation," Biol Blood Marrow Transplant, 18: pp. 1150-1163 (2012).
Maximino Rezende et. al. "Inhibition of 5-lipoxygenase alleviates graft-versus-host disease", J. Exp. Med. vol. 214 No. 11, 3399-3415 (2017).
Muller et al., "Detection of components renal allograft rejection by complement C5A and TCC in plasma and urine," J Lab Clin Med.1997;129(1):62-71 (1997).
Notice of Reasons for Rejection, Japanese Patent Application No. 2017-563314, English translation of Notice of Reasons for Rejection, dated Oct. 1, 2019, 4 pages.
Takatsuka, et. al.,"Predicting the severity of intestinal graft-versus-host disease from leukotriene B4 levels after bone marrow transplantation" Bone Marrow Transplantation 26, 1313-1316 (2000).
Neston-Davies et al., 4280 Clinical and Immunological Characterisation of Coversin, a Novel Small Protein Inhibitor of Complement C5 with Potential As a Therapeutic Agent in PNH and Other Complement Mediated Disorders, 56th ASH Annual Meeting and Exposition Abstracts and Program, (2014), Article.4280 (p. 1-2).
Weston-Davies et al: "Phase I Clinical Trial of Coversin, a novel C5 and LTB4 inhibitor", 7th International Conference on Complement Therapeutics Aegean Conferences, Jun. 9, 2014 (Jun. 9, 2014), pp. 1-17.
Kwan et al, Antigen-presenting cell-derived complement modulates graft-versus-host disease, J Clin Invest, 2012, 122 (6):2234-2238.

\* cited by examiner

FIG. 2

| | |
|---|---|
| ATGCTGGTTTTGGTCACCCTGATTTTCTCCTTTTCTGCAAACATGGCATATGCTGACAGC | 60 |
| M  L  V  L  V  T  L  I  F  S  F  S  A  N  M  A  Y  A  D  S | 20 |
| GAAGGCGACTGCACTGGAAGCGAACCTGTTGACGCTTCCAAGCTTCAGTGAGGGCAAA | 120 |
| E  S  D  C  T  G  S  E  P  V  D  A  F  Q  A  F  S  E  G  K | 40 |
| GAGGCATATGTCCTGGTGAGGTCCACGGATCCAAAGGCCAGGGACTGCTTGAAGGACAA | 180 |
| E  A  Y  V  L  V  R  S  T  D  P  K  A  R  D  C  L  K  E  E | 60 |
| CCAGCCGGAGAAAAGCAAGATAATCTGCCGGTGATGATGACAGTTGAAGAATGGCACA | 240 |
| P  A  G  E  K  Q  D  N  T  L  P  V  M  M  T  F  K  N  G  T | 80 |
| GACTCGGGCTTCAACGGATTGCACGTTTTACTTTTGACGGGGCAAAGGTAAGGCAACCCTT | 300 |
| D  W  A  S  T  D  W  T  F  T  L  D  G  A  K  V  T  A  T  L | 100 |
| GGTAACCTAACCCAAAATAGGAGAAGTCCTCTACGACTCATCACTACTGCCACGTT | 360 |
| G  N  L  T  Q  N  R  E  V  V  Y  D  S  H  H  C  H  V | 120 |
| GACAAGGTCGAAGAGAAGTTCCAGATTATGAGATGGATGTCGATGCGGGAGGCTT | 420 |
| D  K  V  E  K  E  V  P  D  Y  E  M  M  L  D  A  G  G  L | 140 |
| GAAGTGGAAGTCGAGTGCTGCCGTCAAAGCTTGGCGTCGTGGCAGACGTTCAACCAA | 480 |
| E  V  E  V  C  C  R  Q  K  L  E  E  L  A  S  G  R  N  Q | 160 |
| ATGTATCCCATCTCAAGGACTGCTAG | 507 |
| M  Y  P  H  L  K  D  C  * | 168 |

ORNITHODOROS MOUBATA COMPLEMENT INHIBITOR FOR USE IN THE TREATMENT OF COMPLEMENT-MEDIATED DISEASES IN PATIENTS WITH C5 POLYMORPHISM

This application is a national phase entry pursuant to 35 U.S.C. § 371 of International Application No. PCT/EP2015/062742, filed Jun. 8, 2015, which claims the benefit of priority of Great Britain Application No. 1410116.6, filed Jun. 6, 2014, each of which is incorporated by reference herein in its entirety for any purpose.

FIELD OF THE INVENTION

The present invention relates to methods of treating and preventing complement-mediated diseases and disorders in subjects with complement C5 polymorphisms.

All documents mentioned in the text and listed at the end of this description are incorporated herein by reference.

BACKGROUND TO THE INVENTION

Polymorphisms are common in all but the most conserved genes in most species. The presence of polymorphisms in genes that are involved in diseases and disorders of human health has led to the advent of personalised medicine. Personalised medicine allows healthcare to be customised to the individual using a variety of tools including molecular genetic analysis. Medical decisions, choice of drugs and/or treatment regimens can be tailored to the individual patient. Diagnostic testing and genotyping can be used to select appropriate and optimal therapies based on the subject's individual responsiveness to particular drugs.

It has recently come to light that certain genetic variants in human C5, or C5 polymorphisms, give rise to a lack of response to certain agents that inhibit the classical complement pathway, the alternative complement pathway and the lectin complement pathway. In one clinical trial of eculizumab in a particular Japanese population of patients with the complement-mediated disorder paroxysmal nocturnal haemoglobinuria (PNH), several patients had a poor response. These patients displayed the C5 polymorphisms c.2653C>T (p.Arg885Cys) or c.2654G>A (p.Arg885His). In this type of situation, a sub-population of patients may be identified who cannot be treated by conventional means, or perhaps cannot be treated at all if there is no alternative drug available, or if all known drugs act by the same mechanism.

In the present case, there is no available alternative treatment for complement-mediated diseases and disorders that are currently treated using eculizumab. There is therefore a need to identify a means of treating the patient sub-population with C5 polymorphisms that render them currently untreatable.

SUMMARY OF THE INVENTION

Surprisingly, the present inventors have found that the tick protein Coversin (also referred to as EV576 and OmCI in the art and herein [25]) can be used to treat and prevent complement-mediated diseases and disorders in subjects with complement C5 polymorphisms.

Accordingly, the invention provides a method of treating or preventing a complement-mediated disease and/or disorder comprising administering to a subject with a complement C5 polymorphism and in need thereof a therapeutically or prophylactically effective amount of an agent that inhibits the classical complement pathway, the alternative complement pathway and the lectin complement pathway.

The invention also provides an agent that inhibits the classical complement pathway, the alternative complement pathway and the lectin complement pathway for treating or preventing a complement-mediated disease and/or disorder in a subject with a complement C5 polymorphism.

The invention also provides a method of treating or preventing a complement-mediated disease and/or disorder comprising the steps of:
a) identifying a subject with a C5 polymorphism; and
b) identifying an agent that inhibits the classical complement pathway, the alternative complement pathway and the lectin complement pathway in said subject; and
c) administering to said subject a therapeutically or prophylactically effective amount of said agent identified in step (b).

The invention also provides an agent that inhibits the classical complement pathway, the alternative complement pathway and the lectin complement pathway for use in a method of treating or preventing a complement-mediated disease and/or disorder, wherein said method of treating or preventing comprising the steps of:
a) identifying a subject with a C5 polymorphism; and
b) identifying an agent that inhibits the classical complement pathway, the alternative complement pathway and the lectin complement pathway in said subject; and
c) administering to said subject a therapeutically or prophylactically effective amount of said agent identified in step (b).

In a further embodiment, the invention provides a method of selecting a subject with a complement-mediated disease or disorder for treatment with a first agent that inhibits the classical complement pathway, the alternative complement pathway and the lectin complement pathway in a subject with a C5 polymorphism, comprising determining the effectiveness of a second agent that inhibits the classical complement pathway, the alternative complement pathway and the lectin complement pathway in said subject, wherein a subject is selected for treatment with the first agent if the second agent shows decreased effectiveness in the subject with a C5 polymorphism.

In yet a further embodiment, the invention provides an agent that inhibits the classical complement pathway, the alternative complement pathway and the lectin complement pathway for treating a complement-mediated disease or disorder, wherein said agent is administered to a subject on the basis the subject having been determined to have a C5 polymorphism.

Complement

The complement system is an essential part of the body's natural defence mechanism against foreign invasion and is also involved in the inflammatory process. More than 30 proteins in serum and at the cell surface are involved in complement system function and regulation. Recently it has become apparent that, as well as the ~35 known components of the complement system which may be associated with both beneficial and pathological processes, the complement system itself interacts with at least 85 biological pathways with functions as diverse as angiogenesis, platelet activation, glucose metabolism and spermatogenesis The complement system is activated by the presence of foreign antigens. Three activation pathways exist: (1) the classical pathway which is activated by IgM and IgG complexes or by recognition of carbohydrates; (2) the alternative pathway which is activated by non-self surfaces (lacking specific regulatory molecules) and by bacterial endotoxins; and (3) the lectin pathway which is activated by binding of manna-binding lectin (MBL) to mannose residues on the surface of a pathogen. The three pathways comprise parallel cascades of events that result in the production of complement activation through the formation of similar C3 and C5 convertases on cell surfaces resulting in the release of acute mediators of inflammation (C3a and C5a) and formation of the membrane attack complex (MAC). The parallel cascades involved in the classical and alternative pathways are shown in FIG. 1.

The classical complement pathway, the alternative complement pathway and the lectin complement pathway are herein collectively referred to as the complement pathways.

Complement C5 Polymorphisms

Several polymorphisms of human C5 have been reported [1-5]. Mutations in the gene encoding C5 have been associated with various pathologies including complement component 5 deficiency, a disease where patients show a propensity for severe recurrent infections. Defects in this gene have also been linked to susceptibility to liver fibrosis and to rheumatoid arthritis. Polymorphisms in human C5 include insertions, deletions, single amino acid substitutions, frame-shifts, truncations and combinations of these changes.

Certain polymorphisms alter the interaction of C5 with inhibitors of complement pathway activation. Certain other polymorphisms alter C5 activity with clinical significance. Polymorphisms affecting Arg885 of wildtype C5 are of interest. Two polymorphisms of particular interest are Arg885Cys (encoded by c.2653C>T) and p.Arg885His (encoded by c.2654G>A), both of which decrease the effectiveness of the mAb eculizumab [4].

The term "C5 polymorphism" is used herein to mean any variant of C5 other than the wild-type C5. In a human subject, the wild-type C5 is the C5 protein with accession number NP_001726.2; version GI:38016947. The term "C5 polymorphism" includes insertions, deletions, single or multiple amino acid substitutions, frame-shifts, truncations and combinations of these changes in the C5 protein.

These polymorphisms can be present as either heterozygous or homozygous polymorphisms, such as heterozygous C5 for a given polymorphism, homozygous for one polymorphism or heterozygous for different polymorphisms.

Polymorphisms of interest include changes to the amino acid sequence of wildtype C5 which are in proximity to, or within the epitope for eculizumab, (i.e. 879KSSKC883, including K879, S880, S881, K882 and/or C883). For example, any change may be in the epitope for eculizumab or up to 10, 9, 8, 7, 6, 5, 4, 3, 2, 1 amino acids to the N- or C-terminus of the epitope for eculizumab.

Preferably, the amino acid change is not within or in proximity to the Coversin binding site of C5. This is believed to be a conserved region atop C5a at the distal end of the highly conserved CUB-C5d-MG8 superdomain of C5.

Of particular interest in the present invention are C5 polymorphisms that decrease the effectiveness of one or more agents that inhibit the classical complement pathway, the alternative complement pathway and the lectin complement pathway in a subject with wild-type C5. By "decrease the effectiveness" it is meant that the agent has an $IC_{50}$ for the polymorphic C5 protein that is at least 2, 3, 4, 5, 6, 7, 8, 9, 10, 20, 30, 40, 50, 100, 1000 or more times greater than the $IC_{50}$ of the same agent for the wild-type C5 protein.

In a preferred embodiment, the C5 polymorphism decreases the effectiveness of one or more agents that inhibit the classical complement pathway, the alternative complement pathway and the lectin complement pathway, but does not decrease the effectiveness of Coversin or functional equivalents thereof. In a further preferred embodiment, the C5 polymorphism decreases the effectiveness of one or more anti-C5 monoclonal antibodies that inhibit the classical complement pathway, the alternative complement pathway and the lectin complement pathway in a subject with wild-type C5, but does not decrease the effectiveness of other agents that inhibit the classical complement pathway, the alternative complement pathway and the lectin complement pathway by binding to C5 without blocking the C5 convertase binding site.

By "does not decrease the effectiveness" it is meant that the $IC_{50}$ of Coversin or other agents that inhibit the classical complement pathway, the alternative complement pathway and the lectin complement pathway by binding to C5 without blocking the C5 convertase binding site, for the wild-type C5 protein is at least 75%, 80%, 85%, 90%, 95%, 96%, 97%, 98%, 99% or 100% of the $IC_{50}$ of Coversin or other agents that inhibit the classical complement pathway, the alternative complement pathway and the lectin complement pathway by binding to C5 without blocking the C5 convertase binding site for the polymorphic C5 protein. The term "does not decrease" also encompasses an increase in effectiveness.

In an alternative embodiment, effectiveness can be measured by measuring the ability of the agent to inhibit complement activation in serum taken from the subject. For example, complement activity in the serum of said subjects can be measured by any means known in the art or described herein, for example the haemolytic assays described in reference [6].

An agent would be considered to inhibit complement activity in said subject if complement activity in the presence of the agent is reduced when compared to a control. By "reduced" in this context it is meant that complement activity in the treated sample is at least 10, 20, 30, 40, 50, 60, 70, 80, 90, or 100%, reduced compared to a control.

In a particular embodiment, the C5 polymorphism decreases the effectiveness of monoclonal antibody agents in inhibiting activation of one or more of the complement pathways. In a particular embodiment, the C5 polymorphism decreases the effectiveness of the monoclonal antibody eculizumab in inhibiting activation of one or more of the complement pathways. In a further embodiment, the C5 polymorphism decreases the effectiveness of agents that inhibit the classical complement pathway, the alternative complement pathway and the lectin complement pathway by blocking the C5 convertase binding site. In a further specific embodiment, the C5 polymorphism is at position Arg885. Specific polymorphisms at this position include Arg885Cys or Arg885His.

Polymorphisms that alter binding the affinity of C5 to known anti-C5 monoclonal antibodies such as eculizumab, Pexelizumab, and/or N19-8, or the effectiveness of peptidic complement inhibitors such as ARC1905 are also of interest in the context of this invention.

Thus, in a specific embodiment the invention provides a method of treating or preventing a complement-mediated disease and/or disorder comprising administering to a subject with a complement C5 polymorphism and in need thereof, a therapeutically or prophylactically effective amount of an agent that inhibits the classical complement pathway, the alternative complement pathway and the lectin complement pathway, wherein the complement C5 polymorphism decreases the effectiveness of agents that inhibit the classical complement pathway, the alternative complement pathway and the lectin complement pathway by blocking the C5 convertase binding site, but does not decrease the effectiveness of agents that inhibit the classical complement pathway, the alternative complement pathway and the lectin complement pathway without blocking the C5 convertase binding site.

Thus, in a specific embodiment the invention provides a method of treating or preventing a complement-mediated disease and/or disorder comprising administering to a subject with a complement C5 polymorphism and in need thereof, a therapeutically or prophylactically effective amount of an agent that inhibits the classical complement pathway, the alternative complement pathway and the lectin complement pathway, wherein the complement C5 polymorphism decreases the effectiveness of monoclonal antibodies that inhibit the classical complement pathway, the alternative complement pathway and the lectin complement pathway but does not decrease the effectiveness of Coversin or functional equivalents of this agent.

In this specific embodiment, the invention also provides a therapeutically or prophylactically effective amount of an agent that inhibits the classical complement pathway, the alternative complement pathway and the lectin complement pathway for treating or preventing a complement-mediated disease and/or disorder in a subject with a complement C5 polymorphism, wherein the complement C5 polymorphism decreases the effectiveness of agents that inhibit the classical complement pathway, the alternative complement pathway and the lectin complement pathway by blocking the C5 binding site, but does not decrease the effectiveness of agents that inhibit the classical complement pathway, the alternative complement pathway and the lectin complement pathway without blocking the C5 binding site.

In this specific embodiment, the invention also provides a therapeutically or prophylactically effective amount of an agent that inhibits the classical complement pathway, the alternative complement pathway and the lectin complement pathway for treating or preventing a complement-mediated disease and/or disorder in a subject with a complement C5 polymorphism, wherein the complement C5 polymorphism decreases the effectiveness of monoclonal antibodies that inhibit the classical complement pathway, the alternative complement pathway and the lectin complement pathway but does not decrease the effectiveness of Coversin or functional equivalents of this agent.

Thus, in a further specific embodiment the invention provides a method of treating or preventing a complement-mediated disease and/or disorder comprising administering to a subject with a complement C5 polymorphism and in need thereof a therapeutically or prophylactically effective amount of an agent that inhibits the classical complement pathway, the alternative complement pathway and the lectin complement pathway, wherein the complement C5 polymorphism is at position Arg885 and wherein the agent is a protein comprising or consisting of amino acids 19 to 168 of the amino acid sequence in SEQ ID NO: 2 or is a functional equivalent of this protein.

In this specific embodiment, the invention also provides a therapeutically or prophylactically effective amount of an agent that inhibits the classical complement pathway, the alternative complement pathway and the lectin complement pathway for treating or preventing a complement-mediated disease and/or disorder in a subject with a complement C5 polymorphism wherein the complement C5 polymorphism is at position Arg 885 and wherein the agent is a protein comprising or consisting of amino acids 19 to 168 of the amino acid sequence in SEQ ID NO: 2 or is a functional equivalent of this protein.

Identifying Subjects for Treatment

The present invention is particularly useful in subjects that have a polymorphism in complement C5. The subject may either be already known to have a C5 polymorphism, or may be suspected of having a C5 polymorphism. A subject may be suspected of having a polymorphism in C5 for example because of clinical signs of a complement-mediated disorder, because of ethnic origin or pedigree with an incidence of C5 polymorphisms, or because of unexpectedly poor response, and/or unexpectedly high response, to an agent that inhibits one of the complement pathways.

The invention may be useful in the sub-population of subjects that have an unexpectedly poor response to one or more agents that inhibit one of the complement pathways. In particular, the invention is useful in sub-population of subjects with a C5 polymorphism that decreases the effectiveness of monoclonal antibody agents in inhibiting activation of one or more of the complement pathways. In a particular embodiment, the C5 polymorphism decreases the effectiveness of the monoclonal antibody eculizumab in inhibiting activation of one or more of the complement pathways.

For example, subjects with two C5 polymorphisms at position Arg885 (c.2653C>T (p.Arg885Cys) and c.2654G>A (p.Arg885His)) do not respond to eculizumab. However, Coversin has been shown to be able to inhibit C5 cleavage and activation of the complement pathways even in these subjects. Coversin interacts with complement C5 protein in a different manner to the known anti-C5 mAbs, and it is therefore expected that Coversin will also be useful in sub-populations of subjects that are not responsive to known anti-C5 mAbs, and in subjects that have other C5 polymorphisms. Coversin binds to C5, which results in stabilization of the global conformation of C5 but does not block the C5 convertase cleavage site [7]. In contrast, eculizumab blocks the C5 convertase binding site [8].

The polymorphisms Arg885Cys and Arg885His are particularly prevalent in subjects of Japanese and Han Chinese origin. Coversin is therefore a particularly advantageous choice of agent in a sub-population with these ethnic origins.

As can be seen from the Examples, these polymorphisms are not limited to subjects of Japanese and Han Chinese origin. Subjects with C5 polymorphisms can also be identified by other routine techniques including molecular genetic analysis of the gene encoding the C5 protein including sequencing of the gene [4]; testing the ability of various agent to inhibit complement activation in the subject as described herein or by other methods known in the art; and/or biochemical analysis of the C5 protein from the subject, including isoelectric focusing and functional detection [9]. In a clinical setting, a subject with a C5 polymorphism may be identified by an unexpectedly poor response to an agent that inhibits the classical complement pathway, the alternative complement pathway and the lectin complement pathway.

It is also anticipated that Coversin will be useful in sub-populations of subject that are unexpectedly sensitive to other agents that inhibit one of the complement pathways. For example, if a polymorphism increases the affinity of another agent, such as eculizumab, for the C5 protein, it may be difficult to dose the agent correctly. Activation of complement must be tightly controlled to prevent damage to the body's own tissues, and therefore Coversin would be a more attractive alternative in this scenario.

Once a subject with a C5 polymorphism has been identified, it is possible to identify an agent that inhibits the classical complement pathway, the alternative complement pathway and the lectin complement pathway in said subject.

In order to identify an agent that inhibits the complement pathways, complement activity in the serum of the subject is assessed in the presence and absence of a variety of agents that inhibit the classical complement pathway, the alternative complement pathway and the lectin complement pathway, as described herein. In one specific embodiment, the agent that inhibits the classical complement pathway, the alternative complement pathway and the lectin complement pathway in said subject is Coversin or a functional equivalent thereof.

Complement activity in the serum of said subjects can be measured by any means known in the art or described herein, for example the haemolytic assays described in reference [10] and/or by using the Quidel CH50 method as referred to in the examples An agent would be considered to inhibit complement activity in said subject if complement activity in the presence of the agent is reduced when compared to a control. By "reduced" in this context it is meant that complement activity in the treated sample is at least 10, 20, 30, 40, 50, 60, 70, 80, 90, 100%, reduced compared to a control.

The invention therefore provides a method of treating or preventing a complement-mediated disease and/or disorder comprising the steps of:

a) identifying a subject with a C5 polymorphism; and b) identifying an agent that inhibits the classical complement pathway, the alternative complement pathway and the lectin complement pathway in said subject; and c) administering to said subject a therapeutically or prophylactically effective amount of said agent identified in step (b).

The invention also provides a therapeutically or prophylactically effective amount of an agent that inhibits the classical complement pathway, the alternative complement pathway and the lectin complement pathway for use in a method of treating or preventing a complement-mediated disease and/or disorder, wherein said method of treating or preventing comprising the steps of:

a) identifying a subject with a C5 polymorphism; and b) identifying an agent that inhibits the classical complement pathway, the alternative complement pathway and the lectin complement pathway in said subject; and c) administering to said subject a therapeutically or prophylactically effective amount of said agent identified in step (b).

In yet a further embodiment, the invention provides an agent that inhibits the classical complement pathway, the alternative complement pathway and the lectin complement pathway in a subject with a C5 polymorphism for treating a complement-mediated disease or disorder, wherein said agent is administered to a subject on the basis of the subject having been determined to have a C5 polymorphism.

In a further specific embodiment, the invention provides agent that inhibits the classical complement pathway, the alternative complement pathway and the lectin complement pathway in a subject with a C5 polymorphism for treating a complement-mediated disease or disorder in a subject, wherein a) a biological sample from said subject is assayed for the presence or absence of a C5 polymorphism, and b) a therapeutically effective amount of said agent is selectively administered to the individual on the basis of the presence of the C5 polymorphism.

In a specific embodiment, the subject with a C5 polymorphism is identified by a lack of response to a monoclonal antibody that inhibits the classical complement pathway, the alternative complement pathway and the lectin complement pathway in wild-type subjects. This sub-population of subjects is referred to as "non-responders". Non-responders can be identified by confirming that serum complement activity is at least 60% of normal serum complement activity in the presence of the monoclonal antibody that inhibits the classical complement pathway, the alternative complement pathway and the lectin complement pathway in a subject with wild-type C5.

Of particular interest in the present invention are subjects that are non-responders to eculizumab, Pexelizumab, N19-8 and/or ARC1095.

In further specific embodiments, the specific C5 polymorphism may be identified or confirmed by sequencing the gene encoding C5 or by other molecular genetic analysis.

In a further embodiment, the invention provides a method of selecting a subject with a complement-mediated disease or disorder for treatment with a first agent that inhibits the classical complement pathway, the alternative complement pathway and the lectin complement pathway in a subject with a C5 polymorphism, comprising determining the effectiveness in said subject of a second agent that inhibits the classical complement pathway, the alternative complement pathway and the lectin complement pathway in a wild-type subject, wherein a subject is selected for treatment if the second agent that inhibits the classical complement pathway, the alternative complement pathway and the lectin complement pathway in a wild-type subject shows decreased effectiveness in the subject with a C5 polymorphism.

Inhibition of the classical complement pathway, the alternative complement pathway and the lectin complement pathway in said subject can be measured by measuring the ability of an agent to prevent complement activation in serum from the subject, as described herein.

In a specific embodiment, the invention provides an agent that inhibits the classical complement pathway, the alternative complement pathway and the lectin complement pathway for treating a complement-mediated disease or disorder, wherein said agent is administered to a subject on the basis of a sample from the subject having been determined to have at least 60% of normal serum complement activity in the presence of an anti-C5 monoclonal antibody that inhibits the classical complement pathway, the alternative complement pathway and the lectin complement pathway in subjects with wild-type C5.

In a further specific embodiment, the invention provides an agent that inhibits the classical complement pathway, the alternative complement pathway and the lectin complement pathway for treating a complement-mediated disease or disorder in a subject, wherein a) a biological sample from said subject is assayed for the presence or absence of at least 60% of normal serum complement activity in the presence of an anti-C5 monoclonal antibody that inhibits the classical complement pathway, the alternative complement pathway and the lectin complement pathway in subjects with wild-type C5, and b) a therapeutically effective amount of said agent is selectively administered to the individual on the basis of the presence of at least 60% of normal serum complement activity in the presence of an anti-C5 monoclonal antibody that inhibits the classical complement pathway, the alternative complement pathway and the lectin complement pathway in subjects with wild-type C5.

By "at least 60% of normal serum complement activity in the presence of an anti-C5 monoclonal antibody" it is meant that the serum complement activity of the subject is at least 60%, at least 70%, at least 80%, at least 90%, at least 95% or more of the serum complement activity of a normal, untreated control subject. The control subject may have wild-type C5 or may be the same subject prior to treatment with the anti-C5 monoclonal antibody.

In some embodiments, the anti-C5 monoclonal antibody is eculizumab, Pexelizumab and/or N19-8.

These methods can be used to identify subjects and populations of subjects who are susceptible to treatment with Coversin and functional equivalents thereof.

Complement-Mediated Diseases and Disorders

Activation of complement must be tightly controlled to prevent damage to the body's own tissues. Failure to control complement activation has been shown to play a role in a variety of diseases including, amongst others, acute pancreatitis, Age Related Macular Degeneration (AMD), atypical haemolytic uremeic syndrome (aHUS), Alzheimer's disease, Huntingdon's disease, Parkinson's disease, allergic encephalomyelitis, allotransplatation, asthma, adult respiratory distress syndrome, influenza, burn injuries, Crohn's disease, glomerulonephritis, haemolytic anaemia, haemodialysis, hereditary angioedema, ischaemia reperfusion injuries, multiple system organ failure, multiple sclerosis, myasthenia gravis, myocardial infarction, paroxysmal nocturnal haemoglobinuria (PNH), psoriasis, rheumatoid arthritis, septic shock, systemic lupus erythematosus, stroke, thrombotic thrombocytopaenicpurpura (TTP), traumatic brain injury, vascular leak syndrome, and transplantation rejection and graft versus host disease (GvHD), as well as various other peripheral nerve disorders and respiratory disorders [11-16].

Peripheral nerve disorders as listed in reference 15 include of post-infective demyelinating polyradiculoneuropathy (Guillain Barré syndrome), Miller Fisher syndrome, acute inflammatory demyelinating polyradiculoneuropathy (AIDP), chronic inflammatory demyelinating polyradiculoneuropathy (CIDP), diabetic neuropathy, uraemic pruritus, multifocal motor neuropathy, paraproteinaemic neuropathy, anti-Hu neuropathy, post-diphtheria demyelinating neuropathy, multiple sclerosis, radiation myelopathy, giant cell arteritis (temporal arteritis), transverse myelitis, motor neurone disease, dermatomyositis.

Respiratory disorders as listed in reference 14 include asthma, including severe and steroid resistant asthma, COPD, immune complex alveolitis including those caused by exposure to organic dusts, moulds, airborne allergens, mineral dust, chemicals etc. Further conditions included in the definition of respiratory disorders include: farmer's lung, pigeon or bird fancier's lung, barn fever, miller's lung, metalworker's lung, humidifier fever, silicosis, pneumoconiosis, asbestosis, byssinosis, berylliosis, mesothelioma, rhinitis, alveolitis or diffuse fibrotic lung disease caused by exposure to systemic or inhaled drugs and chemical agents including but not limited to: bleomycin, mitomycin, penicillins, sulphonamides, cephalosporins, aspirin, NSAIDs, tartrazine, ACE inhibitors, iodine containing contrast media, non-selective β blocking drugs, suxamethonium, hexamethonium, thiopentone, amiodarone, nitrofurantoin, paraquat, oxygen, cytotoxic agents, tetracyclines, phenytoin, carbamazepine, chlorpropamide, hydralazine, procainamide, isoniazid, p-aminosalicylic acid. Furthermore, the term includes physical lung damage including but not limited to: crush injury, smoke and hot gas inhalation, blast injury, radiation injury, aspiration pneumonitis, lipoid pneumonia; lung damage associated with organ transplantation including but not limited to: cardiac transplantation, lung transplantation, bone marrow transplantation. Also included within the definition of respiratory disorder are cryptogenic fibrosing alveolitis, allergic granulomatosis (Churg-Strauss syndrome), wegener's granulomatosis, broncheolitis obliterans, interstitial pulmonary fibrosis, cystic fibrosis. Also included are respiratory manifestations of autoimmune and connective tissue diseases including but not limited to: rheumatoid disease, systemic lupus erythematosus, systemic sclerosis, polyarteritis nodosa, polymyositis, dermatomyositis, sjögren's syndrome, ankylosing spondylitis, caplan's syndrome, goodpasture's syndrome, pulmonary alveolar proteinosis, idiopathic pulmonary haemosiderosis, histiocytosis X, pulmonary infiltration with eosinophilia (PIE) including but not limited to: simple pulmonary eosinophilia, prolonged pulmonary eosinophilia, asthmatic bronchopulmonary eosinophilia, allergic bronchopulmonary aspergillosis, aspergilloma, invasive aspergillosis, tropical pulmonary eosinophilia, hypereosinohilic syndrome, parasitic infestation and lymphangioleiomyomatosis (LAM).

Of particular interest in the present invention are paroxysmal nocturnal haemoglobinuria (PNH), graft versus host disease (GvHD), thrombotic thrombocytopaenicpurpura (TTP) and atypical haemolytic uremeic syndrome (aHUS).

Agent to be Used in the Invention

In one aspect of the invention, the agent may bind complement C5, including complement C5 from subjects with complement C5 polymorphisms. The agent may act to prevent the cleavage of complement C5, including complement C5 from subjects with complement C5 polymorphisms, by C5 convertase into complement C5a and complement C5b-9. The agent may act to reduce C5a levels in a subject compared to an untreated subject.

In one aspect of the invention, the agent that inhibits the classical complement pathway, the alternative complement pathway and the lectin complement pathway binds to C5 in such a way as to stabilize the global conformation of C5 but not block the C5 convertase cleavage site. Binding of Coversin to C5 results in stabilization of the global conformation of C5 but does not block the convertase cleavage site.

The complement C5 protein, also referred to herein as C5, is cleaved by the C5 convertase enzyme, itself formed from C3a, an earlier product of the alternative pathway (FIG. 1). The products of this cleavage include an anaphylatoxin C5a and a lytic complex C5b-9 also known as membrane attack complex (MAC). C5a is a highly reactive peptide implicated in many pathological inflammatory processes including neutrophil and eosinophil chemotaxis, neutrophil activation, increased capillary permeability and inhibition of neutrophil apoptosis [17].

MAC is associated with other important pathological processes including rheumatoid arthritis [18;19], proliferative glomerulonephritis [20], idiopathic membranous nephropathy [21], proteinurea [22], demyelination after acute axonal injury [23] and is also responsible for acute graft rejection following xenotransplantation [24].

Monoclonal antibodies and small molecules that bind and inhibit C5 have been developed to treat various diseases [12], in particular PNH, psoraiasis, rheumatoid arthritis, systemic lupus erythematosus and transplant rejection. However, these monoclonal antibodies do not bind to certain C5 proteins from subjects with C5 polymorphisms, and are thus ineffective in these subjects [4].

In contrast, the Coversin, and functional equivalents thereof, inhibit complement C5 cleavage both in subjects with wild-type C5 and in subjects with C5 polymorphisms.

The ability of an agent to bind C5, including C5 from subjects with C5 polymorphisms, may be determined by standard in vitro assays known in the art, for example by western blotting following incubation of the protein on the gel with labelled C5. Preferably, the agent according to the invention binds C5, either wild-type and/or C5 from subjects with C5 polymorphisms, with an $IC_{50}$ of less than 0.2 mg/ml, preferably less than 0.1 mg/ml, preferably less than 0.05 mg/ml, preferably less than 0.04 mg/ml, preferably less than 0.03 mg/ml, preferably 0.02 mg/ml, preferably less than 1 µg/ml, preferably less than 100 ng/ml, preferably less than 10 ng/ml, more preferably still, less than 1 ng/ml. The agent need not have the same affinity for wild-type C5 and C5 from subjects with C5 polymorphisms. It may show higher, lower or the same affinity for wild-type C5 and C5 from subjects with C5 polymorphisms.

The ability of an agent to inhibit complement activation may be determined by measuring the ability of the agent to inhibit complement activation in serum. For example, complement activity in the serum can be measured by any means known in the art or described herein.

According to one embodiment of the invention, the agent that binds C5 is not an anti-C5 monoclonal antibody.

The invention also provides a method of treating or preventing a complement-mediated disease and/or disorder in a subject with a complement C5 polymorphism comprising administering to a subject in need thereof a therapeutically or prophylactically effective amount of an agent that inhibits eicosanoid activity.

The invention also provides a therapeutically or prophylactically effective amount of an agent that inhibits eicosanoid activity for treating or preventing a complement-mediated disease and/or disorder in a subject with a complement C5 polymorphism.

The agent according to this aspect of the invention may inhibit leukotrine B4 (LTB4) activity. In particular, the agent according to this aspect of the invention may bind LTB4. The ability of an agent to bind LTB4 may be determined by standard in vitro assays known in the art, for example by western blotting following incubation of the protein on the gel with labelled LTB4. The agent according to the invention may bind LTB4 with an $IC_{50}$ of less than 0.2 mg/ml, preferably less than 0.1 mg/ml, preferably less than 0.05 mg/ml, preferably less than 0.04 mg/ml, preferably less than 0.03 mg/ml, preferably 0.02 mg/ml, preferably less than 1 µg/ml, preferably less than 100 ng/ml, preferably less than 10 ng/ml, more preferably still, less than 1 ng/ml.

In one aspect, the invention provides a method of treating or preventing a complement-mediated disease and/or disorder in a subject with a complement C5 polymorphism comprising administering to a subject in need thereof a therapeutically or prophylactically effective amount of an agent that:

a) inhibits the classical complement pathway, the alternative complement pathway and the lectin complement pathway; and/or b) inhibits eicosanoid activity.

The invention also provides an agent that inhibits:

a) the classical complement pathway, the alternative complement pathway and the lectin complement pathway; and/or b) eicosanoid activity, for treating or preventing a complement-mediated disease and/or disorder in a subject with a complement C5 polymorphism.

According to one embodiment of this aspect of the invention, the agent binds all of C5, C5 from subjects with C5 polymorphisms, and LTB4. The agent according to this embodiment may thus act to prevent the cleavage of complement C5 by C5 convertase into complement C5a and complement C5b-9 (MAC), and also to inhibit LTB4 activity. Using an agent which binds to both C5 and LTB4 is particularly advantageous. C5 and the eicosanoid pathway are both believed to contribute to the observed pathology in many complement-mediated diseases and disorders. Thus by using a single agent which inhibits multiple pathways involved in the inflammatory effects of complement-mediated diseases and disorders, an enhanced effect can be achieved, compared to using an agent which inhibits only a single pathway involved in the inflammatory effects of complement-mediated diseases and disorders. There are furthermore practical advantages associated with administering a single molecule.

Preferably, the agent of the invention is derived from a haematophagous arthropod. The term "haematophagous arthropod" includes all arthropods that take a blood meal from a suitable host, such as insects, ticks, lice, fleas and mites. Preferably, the agent is derived from a tick, preferably from the tick *Ornithodoros moubata*.

According to one embodiment of the invention, the agent is a protein comprising amino acids 19 to 168 of the amino acid sequence in FIG. 2 (SEQ ID NO: 2) or is a functional equivalent of this protein. The agent may be a protein consisting of amino acids 19 to 168 of the amino acid sequence in FIG. 2 or be a functional equivalent of this protein.

According to an alternative embodiment, the protein used according to this embodiment of the invention may comprise or consist of amino acids 1 to 168 of the amino acid sequence in FIG. 2 (SEQ ID NO: 2), or be a functional equivalent thereof. The first 18 amino acids of the protein sequence given in FIG. 2 form a signal sequence which is not required for C5 binding or for LTB4 binding activity and so this may optionally be dispensed with, for example, for efficiency of recombinant protein production.

The protein having the amino acid sequence given in FIG. 2, also referred to herein as the Coversin protein, was isolated from the salivary glands of the tick *Ornithodoros moubata*. Coversin is an outlying member of the lipocalin family and is the first lipocalin family member shown to inhibit complement activation. The Coversin protein inhibits the alternative, classical and lectin complement pathways by binding C5 and preventing its cleavage by C5 convertase into Complement C5a and Complement C5b-9, thus inhibiting both the action of C5a peptide and the MAC. The Coversin protein also binds LTB4. The term "Coversin protein", as used herein, refers to the sequence given in FIG. 2 with or without the signal sequence.

The Coversin protein and the ability of this protein to inhibit complement activation has been disclosed in [25], where the Coversin protein was referred to as the "OmCI protein". The Coversin protein has also been shown to be effective in the treatment of myasthenia gravis [13], respiratory disorders [14] and peripheral nerve disorders [15]. The ability of the Coversin protein to bind eicosanoids including LTB4 and its use in the treatment of diseases mediated by a leukotriene or hydroxyeicosanoid has been suggested in [26]. None of these disclosures suggest that the Coversin protein could be useful in the treatment or prevention of complement-mediated disorders in subjects with a C5 polymorphism.

It has now been found that the Coversin protein is surprisingly effective in the treatment and prevention of complement-mediated disorders in subjects with a C5 polymorphism. The data presented herein demonstrate that, in a subject with an Arg885His polymorphism, inhibition of complement activity in vitro was resistant to eculizumab (30% or 30-80% complement inhibition at best) but completely sensitive to Coversin, with 100% inhibition at all concentrations tested.

Eculizumab therefore does not fully inhibit complement activity in serum from patients with an Arg885His polymorphism, and these patients received no clinical benefit from therapeutic treatment with eculizumab. These data show that complement inhibition in treatment of complement related disorders (for example PNH treatment) with eculizumab is inadequate to see a clinical benefit. On the contrary, Coversin has been shown to retain normal effectiveness in reducing complement activity in serum from patients with this polymorphism and to exhibit effectiveness in the case studies (see Examples 2, 3 and 4). This suggests that the inhibition of complement as seen, for example, with Coversin, gives rise to clinical benefit, for example a clinical benefit may be observed when complement inhibition is at the level that may be achieved by Coversin.

According to a further embodiment of the invention, the agent may be a nucleic acid molecule encoding the Coversin protein or a functional equivalent thereof. For example, gene therapy may be employed to effect the endogenous production of the Coversin protein by the relevant cells in the subject, either in vivo or ex vivo. Another approach is the administration of "naked DNA" in which the therapeutic gene is directly injected into the bloodstream or into muscle tissue.

Preferably, such a nucleic acid molecule comprises or consists of bases 55 to 507 of the nucleotide sequence in FIG. 2 (SEQ ID NO: 1). This nucleotide sequence encodes the Coversin protein in FIG. 2 without the signal sequence. The first 54 bases of the nucleotide sequence in FIG. 2 encode the signal sequence which is not required for complement inhibitory activity or LTB4 binding activity. Alternatively, the nucleic acid molecule may comprise or consist of bases 1 to 507 of the nucleic acid sequence in FIG. 2, which encodes the protein with the signal sequence.

The Coversin protein has been demonstrated to bind to C5 and prevent its cleavage by C5 convertase in rat, mouse and human serum with an $IC_{50}$ of approximately 0.02 mg/ml. Preferably, functional equivalents of the Coversin protein which retain the ability to bind C5 with an $IC_{50}$ of less than 0.2 mg/ml, preferably less than 0.1 mg/ml, preferably less than 0.05 mg/ml, preferably less than 0.02 mg/ml, preferably less than 1 µg/ml, preferably less than 100 ng/ml, preferably less than 10 ng/ml, more preferably still, less than 1 ng/ml.

The Coversin protein has also been demonstrated to bind LTB4. Functional equivalents of the Coversin protein may also retain the ability to bind LTB4 with a similar affinity as the Coversin protein.

In one respect, the term "functional equivalent" is used herein to describe homologues and fragments of the Coversin protein which: a) retain its ability to bind C5, either wild-type C5 or C5 from a subject with a C5 polymorphism, and to prevent the cleavage of complement C5 by C5 convertase into complement C5a and complement C5b-9; and/or b) retain its ability to bind LTB4.

The term "functional equivalent" also refers to molecules that are structurally similar to the Coversin protein or that contain similar or identical tertiary structure, particularly in the environment of the active site or active sites of the Coversin protein that binds to C5, either wild-type C5 or C5 from a subject with a C5 polymorphism, and/or LTB4, such as synthetic molecules. Amino acids in Coversin that are likely to be required for LTB4 binding are described in [26].

The term "homologue" is meant to include reference to paralogues and orthologues of the Coversin sequence that is explicitly identified in FIG. 2, including, for example, the Coversin protein sequence from other tick species, including *Rhipicephalus appendiculatus*, *R. sanguineus*, *R. bursa*, *A. americanum*, *A. cajennense*, *A. hebraeum*, *Boophilus microplus*, *B. annulatus*, *B. decoloratus*, *Dermacentor reticulatus*, *D. andersoni*, *D. marginatus*, *D. variabilis*, *Haemaphysalis inermis*, *Ha. leachii*, *Ha. punctata*, *Hyalomma anatolicum anatolicum*, *Hy. dromedarii*, *Hy. marginatum marginatum*, *Ixodes ricinus*, *I. persulcatus*, *I. scapularis*, *I. hexagonus*, *Argas persicus*, *A. reflexus*, *Ornithodoros erraticus*, *O. moubata moubata*, *O. m. porcinus*, and *O. savignyi*. The term "homologue" is also meant to include the equivalent Coversin protein sequence from mosquito species, including those of the *Culex*, *Anopheles* and *Aedes* genera, particularly *Culex quinquefasciatus*, *Aedes aegypti* and *Anopheles gambiae*; flea species, such as *Ctenocephalides felis* (the cat flea); horseflies; sandflies; blackflies; tsetse flies; lice; mites; leeches; and flatworms. The native Coversin protein is thought to exist in *O. moubata* in another three forms of around 18 kDa and the term "homologue" is meant to include these alternative forms of Coversin.

Methods for the identification of homologues of the Coversin sequence given in FIG. 2 will be clear to those of skill in the art. For example, homologues may be identified by homology searching of sequence databases, both public and private. Conveniently, publicly available databases may be used, although private or commercially-available databases will be equally useful, particularly if they contain data not represented in the public databases. Primary databases are the sites of primary nucleotide or amino acid sequence data deposit and may be publicly or commercially available. Examples of publicly-available primary databases include the GenBank database (http://www.ncbi.nlm.nih.gov/), the EMBL database (http://www.ebi.ac.uk/), the DDBJ database (http://www.ddbj.nig.acjp/), the SWISS-PROT protein database (http://expasy.hcuge.ch/), PIR (http://pir.georgetown.edu/), TrEMBL (http://www.ebi.ac.uk/), the TIGR databases (see http://www.tigr.org/tdb/index.html), the NRL-3D database (http://www.nbrfa.georgetown.edu), the Protein Data Base (http://www.rcsb.org/pdb), the NRDB database (ftp://ncbi.nlm.nih.gov/pub/nrdb/README), the OWL database (http://www.biochem.ucl.ac.uk/bsm/dbbrowser/OWL/) and the secondary databases PRO SITE (http://expasy.hcuge.ch/sprot/prosite.html), PRINTS (http://iupab.leeds.ac.uk/bmb5dp/prints.html), Profiles (http://ulrec3.unil.ch/software/PFSCAN_form.html), Pfam (http://www.sanger.ac.uk/software/pfam), Identify (http://dna.stanford.edu/identify/) and Blocks (http://www.blocks.fhcrc.org) databases. Examples of commercially-available databases or private databases include PathoGenome (Genome Therapeutics Inc.) and PathoSeq (previously of Incyte Pharmaceuticals Inc.).

Typically, greater than 30% identity between two polypeptides (preferably, over a specified region such as the active site) is considered to be an indication of functional equivalence and thus an indication that two proteins are homologous. Preferably, proteins that are homologues have a degree of sequence identity with the Coversin protein sequence identified in FIG. 2 (SEQ ID NO:2) of greater than 60%. More preferred homologues have degrees of identity of greater than 70%, 80%, 90%, 95%, 98% or 99%, respectively with the Coversin protein sequence given in FIG. 2 (SEQ ID NO:2). Percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Functional equivalents of the Coversin protein sequence given in FIG. 2 include mutants containing amino acid substitutions, insertions or deletions from the wild type sequence, for example, of 1, 2, 3, 4, 5, 7, 10 or more amino acids, provided that such mutants retain the ability to bind wild-type C5 and/or C5 from subjects with a C5 polymorphism. Mutants thus include proteins containing conservative amino acid substitutions that do not affect the function or activity of the protein in an adverse manner. This term is also intended to include natural biological variants (e.g. allelic variants or geographical variations within the species from which the Coversin proteins are derived). Mutants with improved ability to bind wild-type C5 and/or C5 from subjects with a C5 polymorphism and/or LTB4 may also be designed through the systematic or directed mutation of specific residues in the protein sequence.

Fragments of the Coversin protein and of homologues of the Coversin protein are also embraced by the term "functional equivalents" providing that such fragments retain the ability to bind wild-type C5 and/or C5 from subjects with a C5 polymorphism and/or LTB4. Fragments may include, for example, polypeptides derived from the Coversin protein sequence which are less than 150 amino acids, less than 125 amino acids, less than 100 amino acids, less than 75 amino acids, less than 50 amino acids, or even 25 amino acids or less, provided that these fragments retain the ability to bind to complement wild-type C5 and/or C5 from subjects with a C5 polymorphism and/or LTB4. Fragments may include, for example, polypeptides derived from the Coversin protein sequence which are at least 150 amino acids, at least 125 amino acids, at least 100 amino acids, at least 75 amino acids, at least 50 amino acids, or at least 25 amino acids, provided that these fragments retain the ability to bind to complement wild-type C5 and/or C5 from subjects with a C5 polymorphism and/or LTB4.

Any functional equivalent or fragment thereof preferably retains the pattern of cysteine residues that is found in Coversin. For example said functional equivalent comprises six cysteine residues that are spaced relative to each other at a distance of 32 amino acids apart, 62 amino acids apart, 28 amino acids apart, 1 amino acid apart and 21 amino acids apart as arranged from the amino terminus to the carboxyl terminus of the sequence according to amino acids 1 to 168 of the amino acid sequence in FIG. 2 (SEQ ID NO:2). Exemplary fragments of Coversin protein are disclosed in SEQ ID NO: 4, SEQ ID NO: 6, SEQ ID NO: 8, SEQ ID NO: 10, SEQ ID NO: 12, SEQ ID NO: 14. The DNA encoding the corresponding fragments are disclosed in SEQ ID NO: 3, SEQ ID NO: 5, SEQ ID NO: 7, SEQ ID NO: 9, SEQ ID NO: 11, SEQ ID NO: 13.

Included as such fragments are not only fragments of the O. moubata Coversin protein that is explicitly identified herein in FIG. 2, but also fragments of homologues of this protein, as described above. Such fragments of homologues will typically possess greater than 60% identity with fragments of the Coversin protein sequence in FIG. 2, although more preferred fragments of homologues will display degrees of identity of greater than 70%, 80%, 90%, 95%, 98% or 99%, respectively with fragments of the Coversin protein sequence in FIG. 2. Fragments with improved may, of course, be rationally designed by the systematic mutation or fragmentation of the wild type sequence followed by appropriate activity assays. Fragments may exhibit similar or greater affinity for C5, either the wild-type or polymorphic variant of C5 or both, and/or LTB4 as Coversin.

A functional equivalent used according to the invention may be a fusion protein, obtained, for example, by cloning a polynucleotide encoding the Coversin protein in frame to the coding sequences for a heterologous protein sequence. The term "heterologous", when used herein, is intended to designate any polypeptide other than the Coversin protein or its functional equivalent. Example of heterologous sequences, that can be comprised in the soluble fusion proteins either at N- or at C-terminus, are the following: extracellular domains of membrane-bound protein, immunoglobulin constant regions (Fc region), multimerization domains, domains of extracellular proteins, signal sequences, export sequences, or sequences allowing purification by affinity chromatography. Many of these heterologous sequences are commercially available in expression plasmids since these sequences are commonly included in the fusion proteins in order to provide additional properties without significantly impairing the specific biological activity of the protein fused to them [27]. Examples of such additional properties are a longer lasting half-life in body fluids, the extracellular localization, or an easier purification procedure as allowed by a tag such as a histidine, GST, FLAG, avidin or HA tag.

The Coversin protein and functional equivalents thereof, may be prepared in recombinant form by expression in a host cell. Such expression methods are well known to those of skill in the art and are described in detail by [28] and [29]. Recombinant forms of the Coversin protein and functional equivalents thereof are preferably unglycosylated.

The proteins and fragments of the present invention can also be prepared using conventional techniques of protein chemistry. For example, protein fragments may be prepared by chemical synthesis. Methods for the generation of fusion proteins are standard in the art and will be known to the skilled reader. For example, most general molecular biology, microbiology recombinant DNA technology and immunological techniques can be found in [28] or [30].

Modes of Administration

Coversin and its functional equivalents do not require a medical professional for administration to be carried out, and these molecules are rapidly absorbed. Many recombinant antibodies are absorbed very slowly and as a result need to be infused over long periods (e.g. intravenously). The administration of such molecules thus also requires a medical professional. Thus, as well as having the advantage of being more effective at inhibiting the activation of the complement pathways in subjects with a C5 polymorphism, Coversin also possesses the advantage of being easier to administer than other agents such as antibodies like eculizumab.

The subject to which the agent is administered in the practice of the invention is preferably a mammal, preferably a human. The subject may be an adult, a child, or an infant. The subject to which the agent is administered may also be suffering from a complement-mediated disease or disorder. In particular, the subject may be known to have, or be suspected of having, a complement C5 polymorphism.

The agent is administered in a therapeutically or prophylactically effective amount. The term "therapeutically effective amount" refers to the amount of agent needed to treat the complement-mediated disease or disorder, as defined elsewhere herein. The term "prophylactically effective amount" used herein refers to the amount of agent needed to prevent complement-mediated disease or disorder as defined elsewhere herein. Preferably, the dose of the agent is sufficient to bind as much available C5 as possible in the subject, more preferably, all available C5. The dose of the agent may alternatively be sufficient to bind as much available LTB4 as possible in the subject, more preferably, all available LTB4. In some aspects, the dose of the agent is sufficient to binds as much available C5 and LTB4 as possible, for example all available C5 and LTB4. The dose of the agent supplied is at least twice the molar dose needed to bind all available C5 and/or LTB4 in the subject. The dose of the agent supplied may be 2.5 times, 3 times or 4 times the molar dose needed to bind all available C5 and/or LTB4 in the subject. Preferably, the dose is from 0.0001 mg/kg (mass of drug compared to mass of patient) to 20 mg/kg, preferably 0.001 mg/kg to 10 mg/kg, preferably 0.01 mg/kg to 2 mg/kg, preferably 0.1 mg/kg to 1 mg/kg; alternatively 0.2 mg/kg to 0.8 mg/kg; alternatively 0.3 mg/kg to 0.7 mg/kg; alternatively 0.4 mg/kg to 0.6 mg/kg; for example 0.14 mg/kg or 0.57 mg/kg. The therapeutically or prophylactically effective amount can additionally be defined in terms of the inhibition of terminal complement, for example, an amount that means that terminal complement activity is reduced by at least 10, 20, 30, 40, 50, 60, 70, 80, 90, 91, 92, 93, 94, 95, 96, 97, 98, 99, 100%, compared to terminal complement activity in the absence of treatment. Dose and frequency may be adjusted in order to maintain terminal complement activity at the desired level, which may be, for example 10% or less, for example 9, 8, 7, 6, 5, 4, 3, 2, 1% or less compared to terminal complement activity in the absence of treatment.

The frequency with which the dose needs to be administered will depend on the half-life of the agent involved. Where the agent is the Coversin protein or a functional equivalent thereof, the dose may be administered as a continuous infusion, in bolus doses or on a daily basis, twice daily basis, or every two, three, four days, five, six, seven, 10, 15 or 20 days or more. As noted elsewhere, a particular advantage of the Coversin protein and its functional equivalents is the relative ease and rapidity with which it can be administered, and the fact that medical professionals are not required for administration.

Single or multiple doses may be administered. For example at least 2, 3, 4, 5, 6, 7, or 8 doses may be administered. Single doses are one embodiment. The exact dosage and the frequency of doses may also be dependent on the patient's status at the time of administration. Factors that may be taken into consideration when determining dosage include the need for treatment or prophylaxis, the severity of the disease state in the patient, the general health of the patient, the age, weight, gender, diet, time and frequency of administration, drug combinations, reaction sensitivities and the patient's tolerance or response to therapy. The precise amount can be determined by routine experimentation, but may ultimately lie with the judgement of the clinician.

The dosage regimen may also take the form of an initial "loading dose" followed by one or more subsequence "maintenance doses". In general, the loading dose will be greater than the maintenance dose. The loading dose may be 2, 5, 10 or more times greater than the maintenance dose. The loading dose may be administered as a single dose, or as one or more doses in a particular time frame. Typically, the loading dose will be 1, 2, 3, 4 or 5 does administered in a single 24 hour period. The maintenance dose will typically be a lower dose that is repeated at regular intervals, such as every 3, 4, 6, 8, 12, 24, or 48 hours. The precise regimen can be determined by routine experimentation, but may ultimately lie with the judgement of the clinician.

The loading dose may be 0.0001 mg/kg (mass of drug compared to mass of patient) to 20 mg/kg, and the maintenance dose may be between 0.0001 mg/kg to 20 mg/kg; alternatively the loading dose is 0.001 mg/kg to 10 mg/kg and the maintenance dose is 0.001 mg/kg to 10 mg/kg, alternatively the loading dose is 0.01 mg/kg to 2 mg/kg and the maintenance dose is 0.01 mg/kg to 2 mg/kg; alternatively the loading dose is 0.1 mg/kg to 1 mg/kg and the maintenance dose is 0.1 mg/kg to 1 mg/kg; alternatively the loading dose is 0.1 mg/kg to 1 mg/kg and the maintenance dose is 0.05 mg/kg to 0.5 mg/kg; alternatively the loading dose is 0.2 mg/kg to 0.8 mg/kg and the maintenance dose is 0.1 mg/kg to 0.4 mg/kg; alternatively the loading dose is 0.3 mg/kg to 0.7 mg/kg and the maintenance dose is 0.1 mg/kg to 0.3 mg/kg; alternatively the loading dose is 0.4 mg/kg to 0.6 mg/kg and the maintenance dose is 0.1 mg/kg to 0.2 mg/kg for example where the loading dose is 0.57 mg/kg and the maintenance dose is 0.14 mg/kg.

The loading dose may be 0.0001 mg/kg (mass of drug compared to mass of patient) to 20 mg/kg, and the maintenance dose may be between 0.0001 mg/kg to 20 mg/kg; alternatively the maintenance dose may be 0.001 mg/kg to 10 mg/kg, alternatively the maintenance dose may be 0.01 mg/kg to 2 mg/kg; alternatively the maintenance dose may be 0.1 mg/kg to 1 mg/kg; alternatively the maintenance dose may be 0.1 mg/kg to 0.8 mg/kg; alternatively the maintenance dose may be 0.1 mg/kg to 0.6 mg/kg; alternatively the maintenance dose may be 0.1 mg/kg to 0.4 mg/kg; alternatively the maintenance dose may be 0.1 mg/kg to 0.2 mg/kg.

The loading dose may be 0.0001 mg/kg (mass of drug compared to mass of patient) to 20 mg/kg, and the maintenance dose may be between 0.0001 mg/kg to 20 mg/kg; alternatively the loading dose may be 0.001 mg/kg to 10 mg/kg, alternatively the loading dose may be 0.01 mg/kg to 2 mg/kg; alternatively the loading dose may be 0.1 mg/kg to 1 mg/kg; alternatively the loading dose may be 0.1 mg/kg to 1 mg/kg; alternatively the loading dose may be 0.2 mg/kg to 0.8 mg/kg; alternatively the loading dose may be 0.3 mg/kg to 0.6 mg/kg; alternatively the loading dose may be 0.4 mg/kg to 0.6 mg/kg. The agent will generally be administered in conjunction with a pharmaceutically acceptable carrier. The term "pharmaceutically acceptable carrier", as used herein, includes genes, polypeptides, antibodies, liposomes, polysaccharides, polylactic acids, polyglycolic acids and inactive virus particles or indeed any other agent provided that the carrier does not itself induce toxicity effects or cause the production of antibodies that are harmful to the individual receiving the pharmaceutical composition. Pharmaceutically acceptable carriers may additionally contain liquids such as water, saline, glycerol, ethanol or auxiliary substances such as wetting or emulsifying agents, pH buffering substances and the like. The pharmaceutical carrier employed will thus vary depending on the route of administration. Carriers may enable the pharmaceutical compositions to be formulated into tablets, pills, dragees, capsules, liquids, gels, syrups, slurries, suspensions to aid intake by the patient. A thorough discussion of pharmaceutically acceptable carriers is available in [31].

The agent may be delivered by any known route of administration. The agent may be delivered locally or systemically. The agent may be delivered by a parenteral route (e.g. by injection, either subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications, needles, and hyposprays.

Preferably the agent is delivered via subcutaneous injection. In some embodiments this is via once daily subcutaneous injection, for example at an initial loading dose of between 0.0001 mg/kg (mass of drug compared to mass of patient) to 20 mg/kg, followed by once daily maintenance doses of between 0.0001 mg/kg to 20 mg/kg, or other doses disclosed elsewhere herein. Alternatively the agent may be delivered via subcutaneous injection every other day.

In a preferred embodiment the agent is delivered via once daily subcutaneous injection at an initial loading dose of 0.4 mg/kg-0.6 mg/kg (for example 0.57 mg/kg) followed by once daily maintenance doses of 0.1 mg/kg-0.2 mg/kg (for example 0.14 mg/kg).

The agent may be administered alone or as part of a treatment regimen also involving the administration of other drugs currently used in the treatment of patients with a complement-mediated disease or disorder.

The agent may be administered simultaneously, sequentially or separately with the other drug(s). For example, the agent may be administered before or after administration of the other drug(s). In particular, the agent may be administered after a pervious drug has failed to threat the complement mediated disease or disorder. In a specific embodiment, the agent may be administered after an anti-C5 monoclonal antibody.

In particular embodiments:
(i) the complement-mediated disease is paroxysmal nocturnal haemoglobinuria (PNH);
(ii) the complement C5 polymorphism is at residue Arg885;
(iii) the agent for treatment is Coversin protein or fragments or homologues of the Coversin protein providing that such fragments retain the ability to bind wild-type C5 and/or C5 from subjects with a C5 polymorphism;
(iv) the agent is delivered subcutaneously.

In certain embodiments the subcutaneous injection is once daily at an initial loading dose of 0.4 mg/kg-0.6 mg/kg (mass of drug compared to mass of patient), followed by once daily maintenance doses of 0.1 mg/kg-0.2 mg/kg; more preferably at an initial loading dose of 0.57 mg/kg (mass of drug compared to mass of patient), followed by once daily maintenance doses of 0.14 mg/kg.

In particular embodiments:
(i) the complement-mediated disease is graft versus host disease (GvHD);
(ii) the complement C5 polymorphism is at residue Arg885;
(iii) the agent for treatment is Coversin protein or fragments or homologues of the Coversin protein providing that such fragments retain the ability to bind wild-type C5 and/or C5 from subjects with a C5 polymorphism;
(iv) the agent is delivered subcutaneously.

In certain embodiments the subcutaneous injection is once daily at an initial loading dose of 0.4 mg/kg-0.6 mg/kg (mass of drug compared to mass of patient), followed by once daily maintenance doses of 0.1 mg/kg-0.2 mg/kg; more preferably at an initial loading dose of 0.57 mg/kg (mass of drug compared to mass of patient), followed by once daily maintenance doses of 0.14 mg/kg.

In particular embodiments:
(i) the complement-mediated disease is thrombotic thrombocytopaenicpurpura (TTP);
(ii) the complement C5 polymorphism is at residue Arg885;
(iii) the agent for treatment is Coversin protein or fragments or homologues of the Coversin protein providing that such fragments retain the ability to bind wild-type C5 and/or C5 from subjects with a C5 polymorphism;
(iv) the agent is delivered subcutaneously.

In certain embodiments the subcutaneous injection is once daily at an initial loading dose of 0.4 mg/kg-0.6 mg/kg (mass of drug compared to mass of patient), followed by once daily maintenance doses of 0.1 mg/kg-0.2 mg/kg; more preferably at an initial loading dose of 0.57 mg/kg (mass of drug compared to mass of patient), followed by once daily maintenance doses of 0.14 mg/kg.

In particular embodiments:
(i) the complement-mediated disease is atypical haemolytic uremeic syndrome (aHUS);
(ii) the complement C5 polymorphism is at residue Arg885;
(iii) the agent for treatment is Coversin protein or fragments or homologues of the Coversin protein providing that such fragments retain the ability to bind wild-type C5 and/or C5 from subjects with a C5 polymorphism;
(iv) the agent is delivered subcutaneously.

In certain embodiments the subcutaneous injection is once daily at an initial loading dose of 0.4 mg/kg-0.6 mg/kg (mass of drug compared to mass of patient), followed by once daily maintenance doses of 0.1 mg/kg-0.2 mg/kg; more preferably at an initial loading dose of 0.57 mg/kg (mass of drug compared to mass of patient), followed by once daily maintenance doses of 0.14 mg/kg.

Various aspects and embodiments of the present invention will now be described in more detail by way of example. It will be appreciated that modification of detail may be made without departing from the scope of the invention.

BRIEF DESCRIPTION OF FIGURES

FIG. 2: Primary sequence of Coversin. Signal sequence underlined. Cysteine residues in bold type. Nucleotide and amino acid number indicated at right. The nucleotide sequence for Coversin is SEQ ID NO: 1. The amino acid sequence for Coversin is SEQ ID NO: 2.

EXAMPLES

Figure 1:
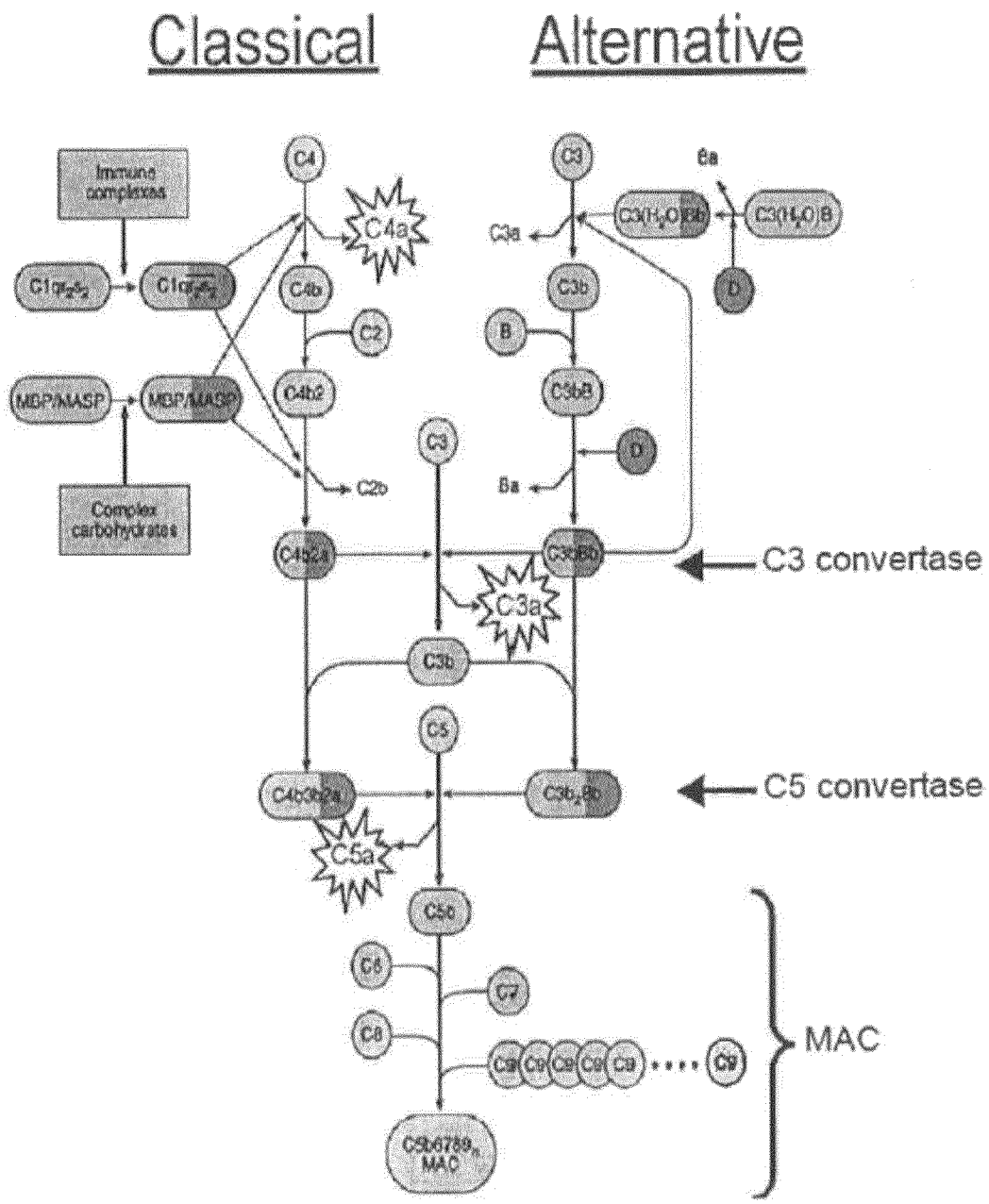
FIG. 1: Schematic diagram of classical and alternative pathways of complement activation. Enzymatic components, dark grey. Anaphylatoxins enclosed in starbursts.

Example 1—In Vitro Inhibition of C5 Activity

Terminal complement activity was measured in serum from a 4 year old, male, Caucasian patient found to have a rare genetic polymorphism in the gene encoding complement C5 (c.2654G>A (p.Arg885His)) by Quidel $CH_{50}$ haemolysis assay.

The Quidel Microvue CH50 Eq enzyme immunoassay (cat #A018) was used is for in vitro measurement of total classical pathway activity in human serum.

The kit provides a direct measure of the terminal complement complex (TCC) formation under standard conditions. Measurement of CH50 with the kit has 3 steps:

1. Activation of the classical complement pathway in undiluted serum resulting in formation of TCC.
2. Dilution of serum and addition to microassay wells coated with an antibody that captures TCC.
3. Quantification of captured TCC with and anti-TCC horse radish peroxidase (HRP) conjugated antibody.

Colour intensity on addition of substrate is proportional to the concentration of TCC present in each reaction. Using the kit standard curve (determined during each assay) assay results are expressed in CH50 unit equivalents per millilitre (CH50 U Eq/ml).

The linear range for the kit is 30-310 U Eq/ml.

According to the manufacturers the cut off for normality determined from 234 individual human samples is 70 CH50 U Eq/ml.

Following treatments with eculizumab, the patient retained 70% complement activity as compared to complement activity in the serum of a normal control with wild-type C5.

Spiking the serum taken after administration of eculizumab with 30, 60 and 120 µg/ml Coversin resulted in undetectable levels of complement activity.

Thus, in a non-responder to eculizumab, Coversin retained normal effectiveness.

Example 2—Case Study

A 4 year old, male, Caucasian patient, weighing 13.6 kg, received a primary diagnosis of chronic granulomatous disease and underwent haematopoietic stem cell transplantation in October 2013. Subsequently the patient developed major gastrointestinal bleeding due to thrombocytopenia and is now receiving daily platelet transfusions. The diagnosis is either graft versus host disease (GvHD) or thrombotic thrombocytopaenicpurpura (TTP).

Treatment with eculizumab, infliximab and rituximab have been unsuccessful.

The patient has been found to have a rare genetic polymorphism in the gene encoding complement C5 (c.2654G>A (p.Arg885His)), previously only described in people of Japanese or Han Chinese origin.

In vitro assays of serum complement activity as described above showed that complement activity result was ~70% haemolytic activity compared to normal control after treatment with eculizumab. In contrast, spiking the serum with Coversin at 30, 60 and 120 µg/ml reduced haemolytic activity to undetectable levels.

Following identification of susceptibility to inhibition of the complement pathways by Coversin, the following treatment was begun:

Coversin, by subcutaneous injection according to the following schedule:

Initial Loading Dose: 0.57 mg/kg=7.8 mg (0.7 ml)

Maintenance Dose: 0.14 mg/kg=1.9 mg (0.2 ml) every 24 hours thereafter

Serum will be taken daily for complement activity and dose and/or frequency will be adjusted in order to maintain terminal complement activity at 10% or less compared to normal control serum.

The following outcomes will also be monitored:
a) Change in trough platelet counts
b) Change in serum LDH
c) Terminal complement activity measured by Quidel $CH_{50}$ haemolysis assay

Example 3—Results of Case Study

The patient of Example 2 was treated with Coversin for about 6 weeks. On the first day of treatment he received a dose calculated to ablate circulating C5 (0.57 mg/kg) and thereafter 50% of this dose until the end of the second week. From then the patient received the same dose every other day for two weeks and then half that dose for a further two weeks. It should be noted that the dose from the third week onwards was likely to have been inadequate to fully control terminal complement activity.

Clinically the patient stabilised during the period that he received the full dose. The main consequence of his illness, which was presumed to be a thrombotic thromocytopaenic purpura (TTP), was severely reduced platelet count for which he had been receiving two units of platelets every day for several months. After 7 days of Coversin treatment the trough platelet counts (approximately 12 hours post platelet transfusion) began to rise reaching 98,000 by Day 14, the highest value that had been recorded throughout his illness.

Figure 3:
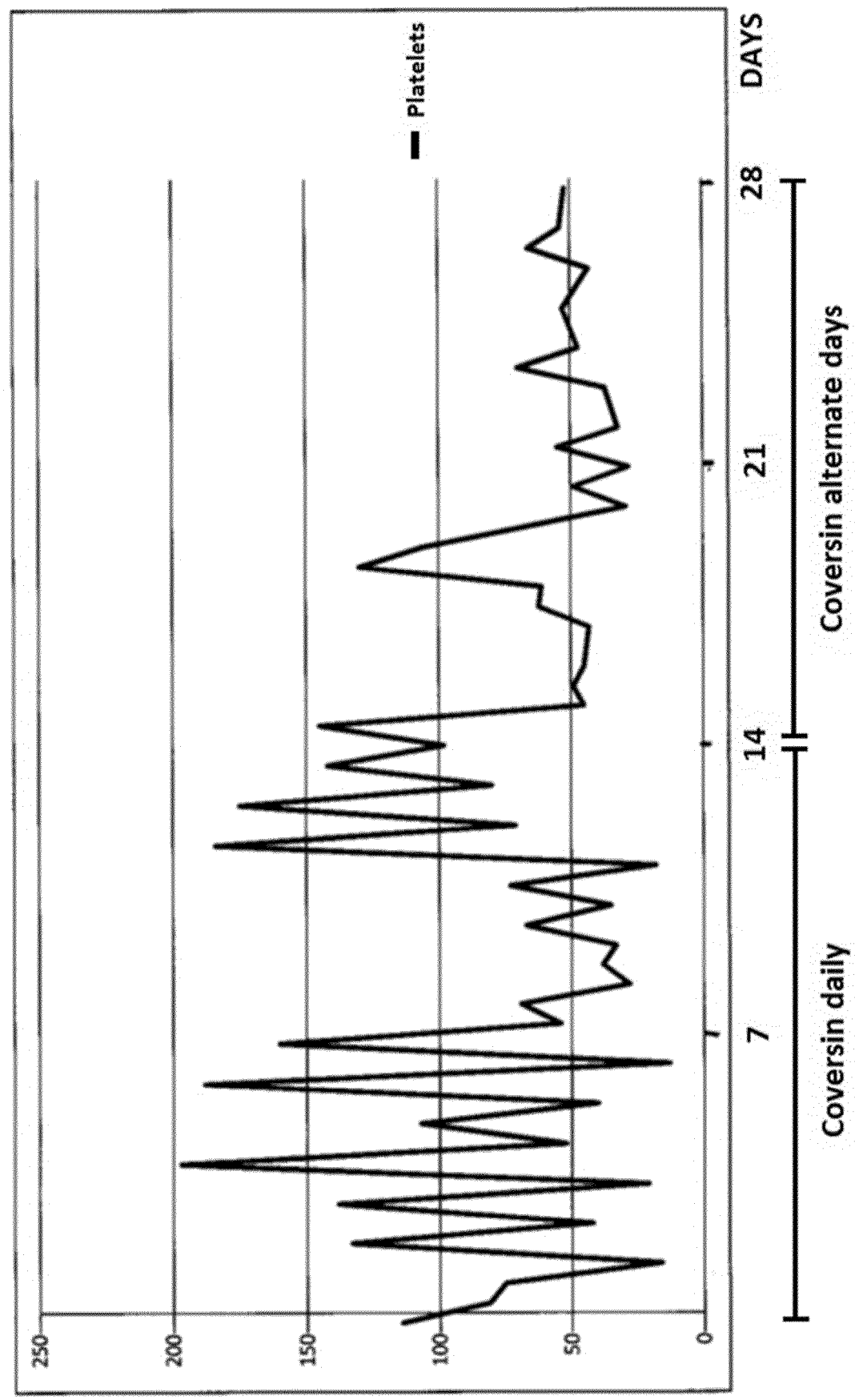
FIG. 3: Peak and trough platelet counts from patient treated in Example 2

His requirement for platelet transfusion was reduced to one unit per day at that point (see FIG. 3).

The dose was reduced at the start of the third week and the trough platelet count fell to below 50,000 and did not recover for the remainder of his illness. The rise in trough platelet count and the reduced need for platelet transfusion was considered by the medical staff as a clear indication of a positive response to Coversin. The deterioration after the dose was reduced seems to confirm this.

The final dose of Coversin was given after 6 weeks and the patient rapidly deteriorated and died from perforation of the jejunum after a further 2 weeks.

Example 4—Case Study

A male patient aged in his mid-forties was diagnosed with PNH and he has been treated with eculizumab for about a year with an inadequate clinical response. Genetic analysis has confirmed a heterozygous C5 polymorphism at position c.2654 but it is not known what amino acid shift this gives rise to although it is known that it is not pArg885His.

Example 5—Terminal Complement Activity in Serum from Patients

Reagents & Samples

Sample Preparation: Serum was prepared by collecting blood into plain glass or SST Vacutainer tubes (or equivalent) and allowing it to clot for 1 hour, before centrifugation at 1500 g for 10 minutes. The serum was separated immediately (avoiding contamination with any blood cells) and stored in screw cap cryotubes (approximately 0.5 ml aliquots) at −70° C.

Coversin: Frozen 10.9 mg/ml solution at −70° C. Dilute 10 uL in 90 uL normal control or patient serum to give a final concentration of 1.09 mg/ml. Dilute 10 uL in 90 uL autologous serum to give a final concentration of 109 ug/ml. Double dilute in autologous serum to achieve a final concentration range of: 0.4-54.5 ug/ml.

Eculizumab: Frozen solution of 10 mg/ml. Dilute 10 uL in 90 uL normal control or patient serum to give a final concentration of 1 mg/ml. Dilute 10 uL in 90 uL autologous serum to give a final concentration of 100 ug/ml. Double dilute in autologous serum to achieve a final concentration range of: 0.4-50 ug/ml.

Buffer: Phosphate Buffered Saline (0.01M phosphate buffer, 0.0027M potassium chloride, 0.137M sodium chloride, pH7.4).

Methods

Coversin, Eculizumab, or buffer (control), are spiked into serum according to the procedure above to achieve a range of final concentrations. These are then assayed for CH50 Equivalent activity using the Quidel CH50 kit, using duplicate wells.

Results

Calculate CH50 values from the calibration curve provided with the kit. Plot the results as raw CH50 values against C5 inhibitor concentration.

Calculate the CH50 result at each C5 inhibitor concentration as a percentage of the CH50 concentration of the relevant buffer control. Plot the percentage CH50 results against inhibitor concentration.

Repeat the experiment on separate days to obtain 3 measurements in each patient and in a single normal control. This provides an estimate of between experiment variability.

Repeat the experiment on separate days in single experiments on 6 different normal controls. This provides an estimate of between subject responsiveness (and avoids the risk of using a single subject who may have an unknown C5 mutation or polymorphism).

The highest dose of each drug to whole serum was added and then two-fold serial dilutions were made in whole serum. One replicate was used for each drug dose.

The highest dose of Eculizumab was 50 µg/ml, then 25, 12.5, 6.3, 3.2, 1.6, 0.8, 0.4 and 0 µg/ml. The highest dose of Coversin was 54.5 µg/ml, then 27.3, 13.1, 6.6. 3.3, 1.7, 0.9 and 0 µg/ml.

After serial dilution the serum was activated and assayed in accordance with the instructions for the Quidel CH50 kit.

CH50 U Eq/ml were calculated in comparison with the kit standards and plotted against drug concentration for each of the three serum samples and two drug treatments. They were also plotted as a percentage of the CH50 value of the relevant buffer only control.

Normal human serum and serum from the patients in the case studies were tested for terminal complement activity in the presence of Eculizumab and Coversin as described above.

Figure 6:
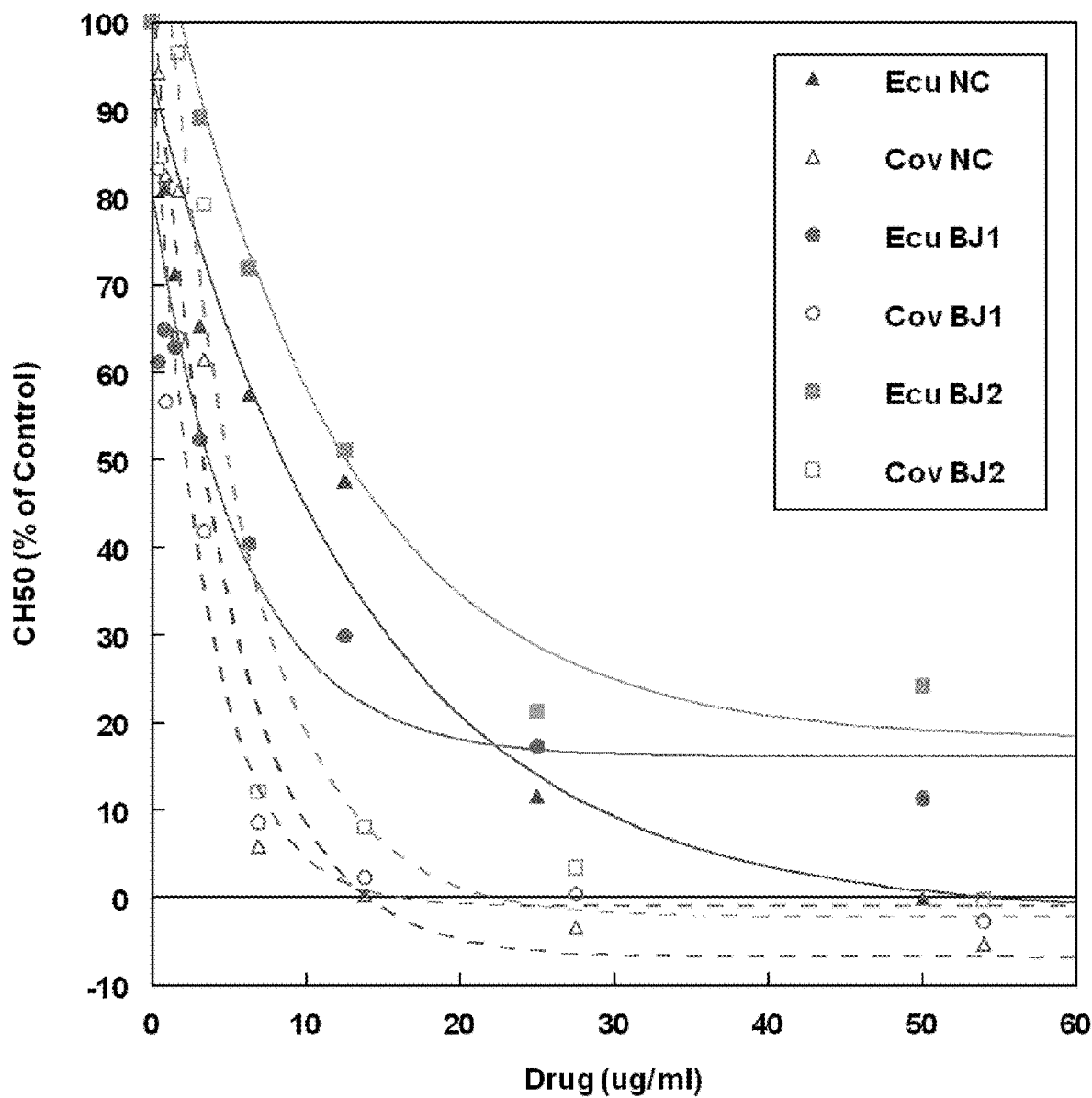
FIG. 6: In vitro testing of serum from patient in Example 3 by CH50 assay after spiking with variable doses of Coversin and eculizumab (expressed as a percentage of control) Shows percentage complement activity from patient in Example 3 compared to control serum in presence of Eculizumab or Coversin. KEY: Ecu, spiked with Eculizumab; Cov, spiked with Coversin. NC, normal control serum; BJ1, replicate 1 using patient serum; BJ2 replicate 2 using patient serum.
Figure 7:
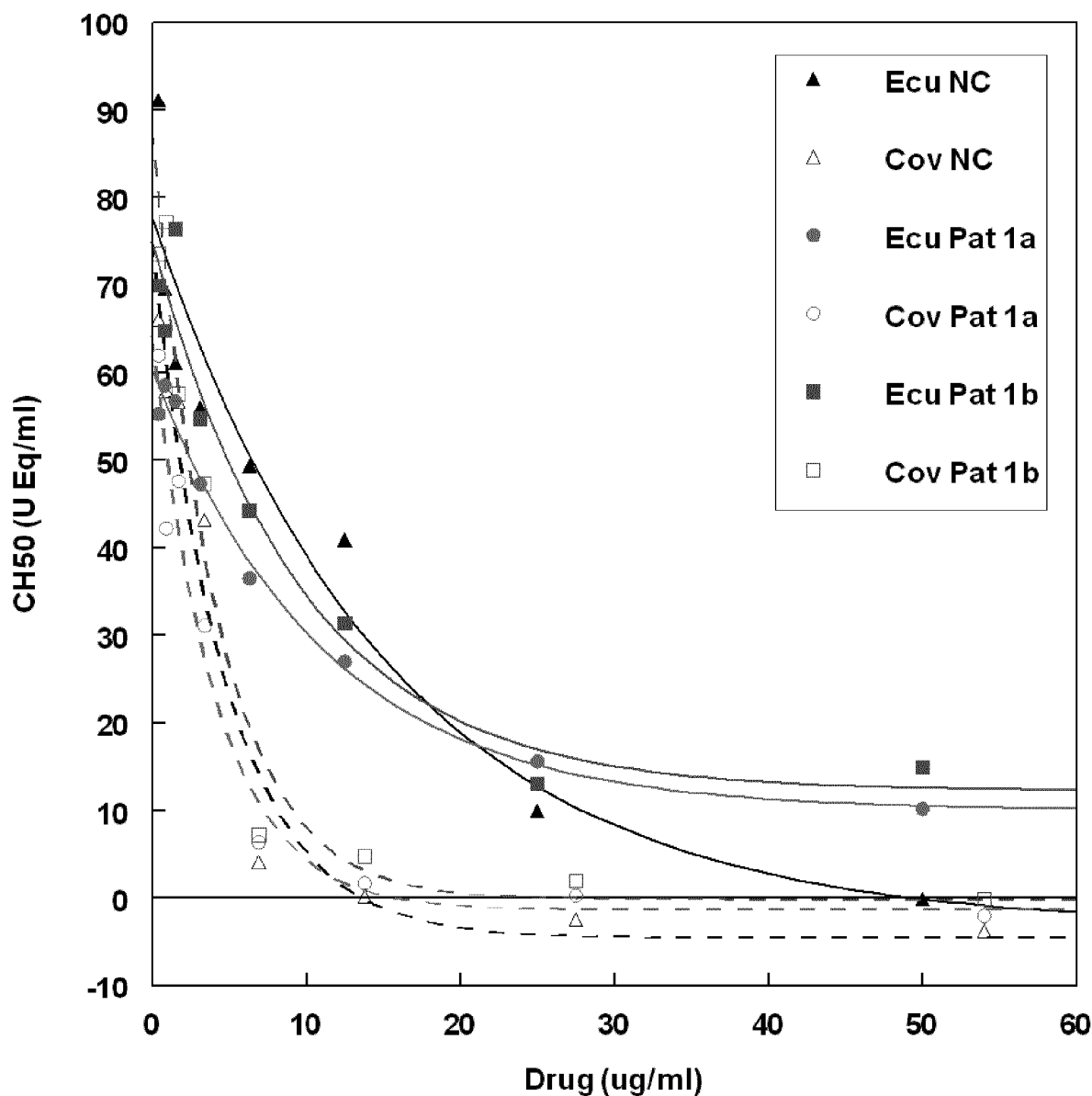
FIG. 7: In vitro testing of serum from patient in Example 3 by CH50 assay after spiking with variable doses of Coversin and eculizumab. Shows complement activity in CH50 Eq/ml units from patient in Example 3 in presence of Eculizumab or Coversin. KEY: Ecu, spiked with Eculizumab; Cov, spiked with Coversin. BJ1 and BJ2 referred to as Pat 1a and Pat 1b.
Figure 8:
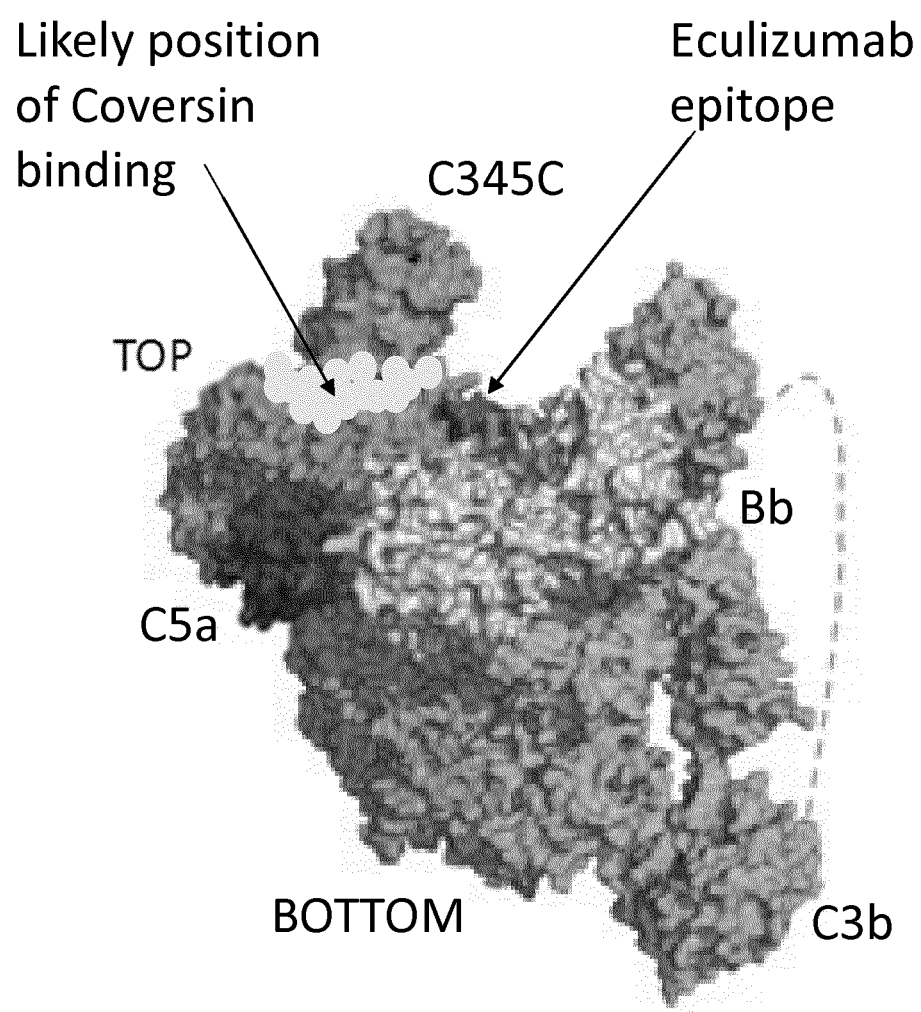
FIG. 8: Molecular model showing the position of the eculizumab epitope and the likely binding site of Coversin

As shown in FIGS. 6 and 7, in the absence of either drug the baseline CH50 values of the normal human serum (average 78.1 CH50 U Eq/ml) and the two patient serum samples from the patient described in the case study of examples 2 and 3 (average 82.4 and 60.6 CH50 U Eq/ml) were within (normal control and BJ 2) or slightly below (BJ 1) the normal human range of >70 CH50 U Eq/ml.

Coversin inhibited both normal human serum and serum from the patient with the p.Arg885His polymorphism equally well. Less than 5% of baseline CH50 (U Eq/ml) was seen at Coversin concentrations of approximately 15 ug/ml.

Eculizumab inhibited normal human serum at the expected dose, with less than 5% of baseline CH50 (U Eq/ml) seen at concentrations of approximately 45 ug/ml. At doses above 25 ug/ml eculizumab inhibited complement activity measured using the Quidel CH50 kit similarly in normal human serum and serum from the patient with the p.Arg885His polymorphism. However, it did not fully inhibit serum from the patient, with approximately 20% of baseline CH50 remaining at the highest dose of eculizumab tested (60 ug/ml).

Figure 4:
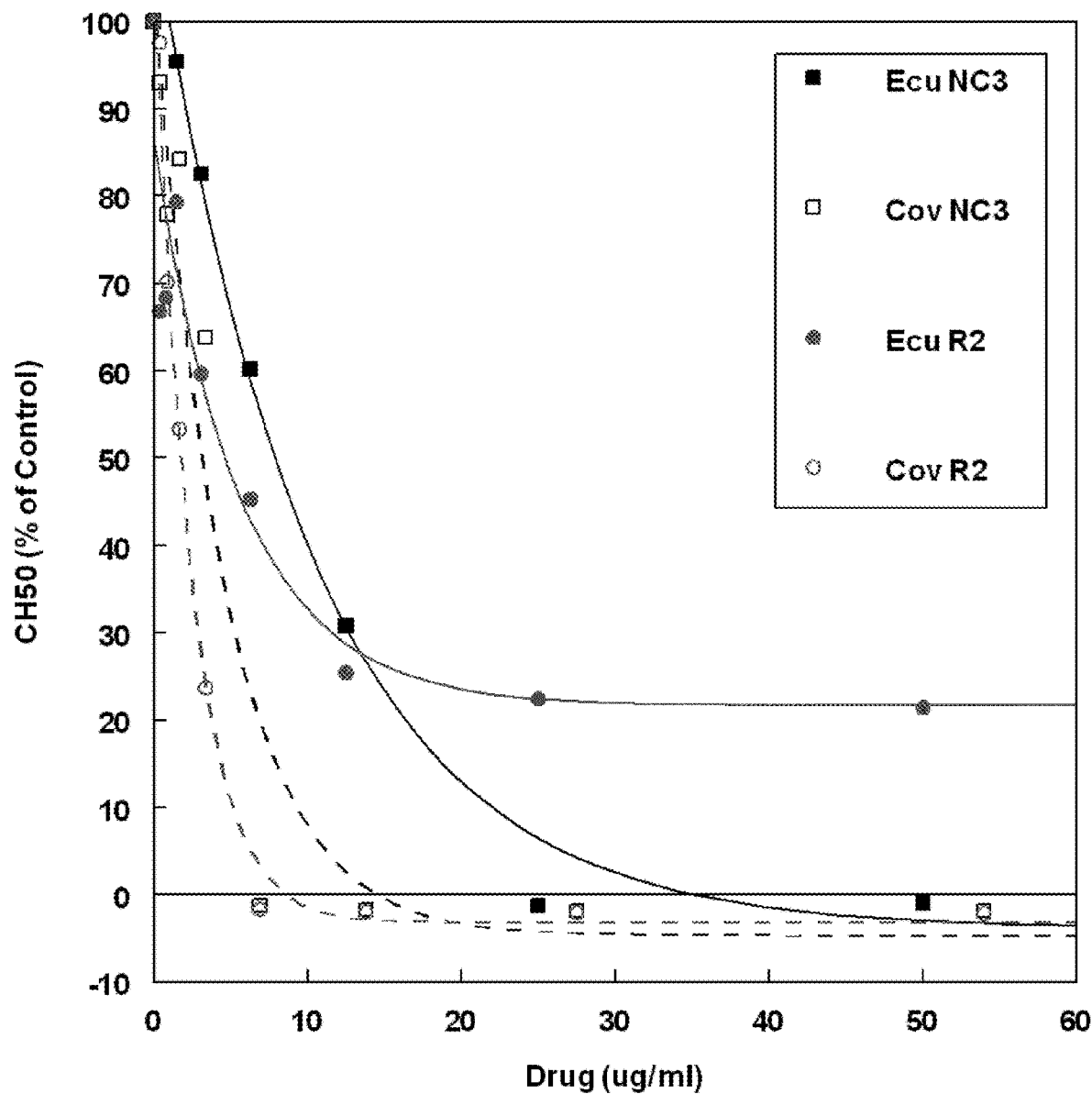
FIG. 4: In vitro testing of serum from patient in Example 4 by CH50 assay after spiking with variable doses of Coversin and eculizumab (expressed as a percentage of control). Shows percentage complement activity in serum from patient in Example 4 compared to control serum in presence of Eculizumab or Coversin. KEY: Ecu, spiked with Eculizumab; Cov, spiked with Coversin. NC3, normal control serum; R2, patient serum.
Figure 5:
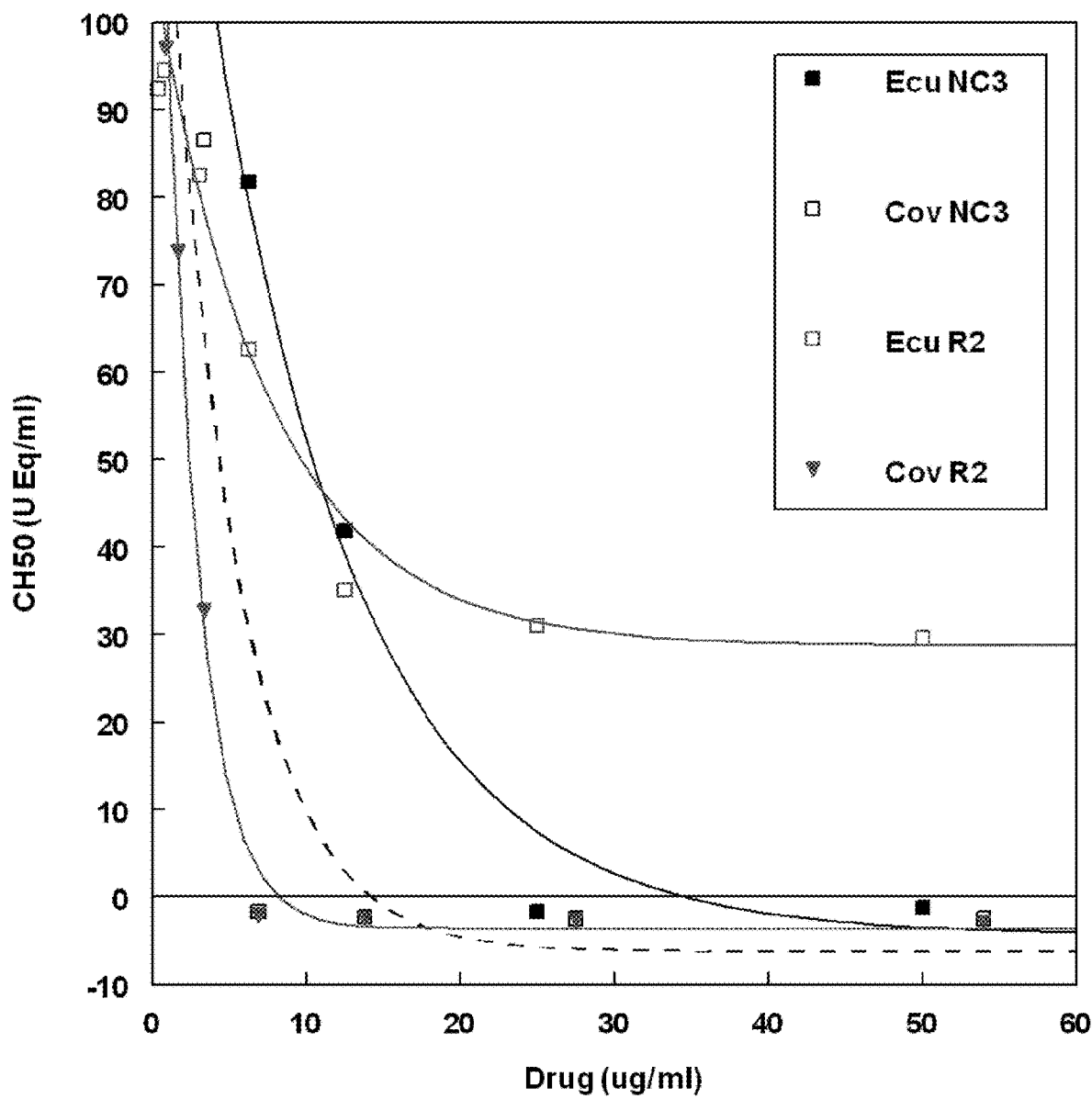
FIG. 5: In vitro testing of serum from patient in Example 4 by CH50 assay after spiking with variable doses of Coversin and eculizumab. Shows complement activity in CH50 Eq/ml units in serum from patient in Example 4 compared to control serum in presence of Eculizumab or Coversin. KEY: Ecu, spiked with Eculizumab; Cov, spiked with Coversin. NC3, normal control serum; R2, patient serum.

Serum from the patient described in Example 4 was also tested in parallel with normal human serum. As shown in FIGS. 4 and 5, in absence of either drug the baseline CH50 values of the normal human serum and the serum from the patient serum samples were within the normal human range of >70 CH50 U Eq/ml.

Coversin inhibited both normal human serum and serum from the patient with an amino acid substitution at Arg885 equally well. Less than 5% of baseline CH50 (U Eq/ml) was seen at Coversin concentrations of approximately 15 ug/ml.

Eculizumab inhibited normal human serum at the expected dose, with less than 5% of baseline CH50 (U Eq/ml) being achieved. Akin to the patient serum from Example 2, at doses above 25 ug/ml eculizumab inhibited complement activity similarly in normal human serum and serum from the Example 4 patient, but it did not completely inhibit serum from the Example 4 patient, with approximately 10% of baseline CH50 remaining at the highest dose of eculizumab tested (50 ug/ml).

Eculizumab does not completely inhibit complement activity in serum from both patients (Example 2 and Example 4) who received no benefit from therapeutic treatment with eculizumab. This supports the hypothesis that complement inhibition in PNH treatment needs to be higher than this to see therapeutic benefit.

Using recombinant expression Nishimura et al. (2014) showed that the C5 p.Arg885His polymorphism seen in the Example 2 patient completely ablates eculizumab binding to C5. The partial inhibition of the Example 2 patient's complement serum by eculizumab shown in the current study (FIGS. 6 and 7) is understandable as the Example 2 patient and all other individuals with the polymorphism identified to date are heterozygotes with a normal copy of C5 and a copy of p.Arg885His C5. If both copies are fully expressed, eculizumab will fully inhibit 50% of the C5 protein present in these individuals. The fact that only 20% residual CH50 activity was seen may reflect the fact that the Example 2 patient was receiving fresh blood products every day which likely increased the ratio of normal C5 to p.Arg885His C5, thus reducing the relative amount of C5 p.Arg885His not inhibited by eculizumab.

Eculizumab appears to inhibit the Example 4 patient's serum to a greater extent than the Example 2 patient's serum, though some residual complement activity remains at even the highest dose of eculizumab. A possible explanation is that the amino acid change at Arg885 is a conservative one that has a less profound effect on eculizumab binding than p.Arg885His.

By contrast, Coversin is an equally effective inhibitor of normal human serum, and the serum from the two patients which are not fully inhibited by eculizumab. Complete inhibition by Coversin is understandable as it likely binds to a different site on C5 than eculizumab. Furthermore Coversin has been shown to be an equally effective inhibitor of C5 in a wide range of mammalian species including man, cynomologus monkey, pig, rat, mouse, rabbit and guinea pig. This indicates that binding of Coversin to C5 is far more tolerant of differences in the amino acid sequence of C5 than eculizumab which is only able to inhibit human C5. Coversin should be considered for treatment of patients that would benefit from C5 inhibition but who gain little or no therapeutic treatment from administration of eculizumab due to polymorphisms in C5 that prevent or reduce the affinity of the binding interaction between eculizumab and C5.

REFERENCES

[1] Pfarr N, et al. J Immunol. 174(7):4172-7. (2005) Erratum in: J Immunol.; 182(8):5152
[2] Delgado-Cerviño E, Fontán G, López-Trascasa M. Mol Immunol. 42(1):105-11. (2005)
[3] Halangk J, et al., J Hepatol. 49(3):339-45 (2008)
[4] Nishimura, J et al., New Engl J. Med., 30; 7: 632-639 (2014)
[5] Wang X, Fleischer D T, Whitehead W T, Haviland D L, Rosenfeld S I, Leddy J P, Snyderman R, Wetsel R A. J Immunol. 154(10):5464-71. (1995)
[6] Jakowski et al., Clin Diagn Lab Immunol. 6(1): 137-139 (1999)
[7] Freslund et al., Nature Immunology 9, 753-760 (2008)
[8] Zuber et al. Nature Reviews Nephrology 8, 643-657
[9] Hobart, M. J., et al., Annals of Human Genetics 45.1 (1981): 1-4.
[10] Jakowski et al., Clin Diagn Lab Immunol. 6(1): 137-139 (1999)
[11] Sahu et al., Immunopharmacology, 49:133-148 (2000).
[12] Ricklin D & Lambris J, Nature Biotechnology, 25: 1265-1275 (2007)
[13] WO 2007/028968
[14] WO 2008/029169
[15] WO 2008/029167
[16] WO 2011/083317
[17] Guo, R. F. and P. A. Ward, Annu Rev Immunol, 2005, 23: p. 821-52
[18] Neumann, E., et al., Arthritis Rheum, 2002. 46(4): p. 934-45
[19] Williams, A. S., et al., Arthritis Rheum, 2004, 50(9): p. 3035-44
[20] Quigg, R. J., Curr Dir Autoimmun, 2004. 7: p. 165-80
[21] Papagianni, A. A., et al., Nephrol Dial Transplant, 2002, 17(1): p. 57-63
[22] He, C., et al., J Immunol, 2005. 174(9): p. 5750-7
[23] Mead, R. J., et al., J Immunol, 2002. 168(1): p. 458-65
[24] Nakashima, S., et al., J Immunol, 2002. 169(8): p. 4620-7
[25] WO 2004/106369
[26] WO 2009/098454
[27] Terpe K, Appl Microbiol Biotechnol, 60: 523-33, 2003
[28] Sambrook et al (2000)
[29] Fernandez & Hoeffler (1998)
[30] Ausubel et al. (1991)
[31] Remington's Pharmaceutical Sciences; Mack Pub. Co., N.J. 1991

The invention claimed is:

1. A method of treating a complement-mediated disease and/or disorder comprising administering to a subject known to have a complement C5 polymorphism and in need thereof a therapeutically effective amount of an agent that inhibits the classical complement pathway, the alternative complement pathway and the lectin complement pathway, wherein the agent is:
   i) a protein comprising an amino acid sequence having at least 90% sequence identity to amino acids 19 to 168 of SEQ ID NO: 2, or
   ii) a protein comprising an amino acid sequence having at least 90% sequence identity to amino acids 1 to 168 of SEQ ID NO: 2, or
   iii) a fragment of the complement inhibitor polypeptide of SEQ ID NO: 2, wherein said fragment comprises six cysteine residues that are spaced relative to each other at a distance of 32 amino acids apart, 62 amino acids apart, 28 amino acids apart, 1 amino acid apart, and 21 amino acids apart as arranged from the amino terminus to the carboxyl terminus of SEQ ID NO: 2;
   and wherein the complement C5 polymorphism is an Arg885 polymorphism and decreases the effectiveness of eculizumab.

2. The method of claim 1, wherein the agent that is administered binds to C5 but does not block the C5 convertase binding site.

3. The method of claim 1, wherein the agent that is administered is a protein comprising or consisting of a sequence at least 95% identical to amino acids 19 to 168 of the amino acid sequence in SEQ ID NO: 2 or a sequence at least 95% identical to amino acids 1 to 168 of the amino acid sequence in SEQ ID NO: 2.

4. The method of claim 1, wherein the agent that is administered is a protein comprising or consisting of amino acids 19 to 168 or 1 to 168 of the amino acid sequence in SEQ ID NO: 2.

5. The method of claim 1, wherein the subject is a mammal.

6. The method of claim 1, wherein the subject is a non-responder to anti-C5 monoclonal antibodies.

7. The method of claim 1, wherein the subject is a human.

8. The method of claim 1, wherein the subject with a complement C5 polymorphism is identified by:
   (a) a poor clinical response to an agent that inhibits at least one of the complement pathways; and/or
   (b) testing the ability of an agent that inhibits at least one of the complement pathways to inhibit complement activation in the subject; and/or
   (c) molecular genetic analysis.

9. The method of claim 1, wherein the subject with a complement C5 polymorphism is identified by a determination that a sample from the subject has at least 60% of normal serum complement activity in the presence of an anti-C5 monoclonal antibody, wherein the anti-C5 monoclonal antibody inhibits, in subjects with wild-type C5, the classical complement pathway, the alternative complement pathway, and the lectin complement pathway.

10. The method of claim 1, wherein the complement C5 polymorphism is identified or confirmed by sequencing the gene encoding C5 or other molecular genetic analysis.

11. The method of claim 1, wherein the subject has a complement-mediated peripheral nerve disorder.

12. The method of claim 1, wherein the subject has a complement-mediated respiratory disorder.

13. The method of claim 1, wherein the subject has a complement-mediated autoimmune disease.

14. The method of claim 1, wherein the subject has a complement-mediated connective tissue disorder.

15. The method of claim 1, wherein the disease and/or disorder comprises paroxysmal nocturnal haemoglobinuria, graft versus host disease, or atypical haemolytic uremic syndrome.

16. The method of claim 1, wherein the complement C5 polymorphism is Arg885Cys or Arg885His.

17. A method of treating a complement-mediated disease and/or disorder comprising:
   a) identifying a subject with a C5 polymorphism, wherein the complement C5 polymorphism is an Arg885 complement C5 polymorphism and decreases the effectiveness of eculizumab; and
   b) administering to the subject a therapeutically effective amount of an agent that inhibits the classical complement pathway, the alternative complement pathway and the lectin complement pathway, wherein the agent is:
   i) a protein comprising an amino acid sequence having at least 90% sequence identity to amino acids 19 to 168 of SEQ ID NO: 2, or
   ii) a protein comprising an amino acid sequence having at least 90% sequence identity to amino acids 1 to 168 of SEQ ID NO: 2, or
   iii) a fragment of the complement inhibitor polypeptide of SEQ ID NO: 2, wherein said fragment comprises six cysteine residues that are spaced relative to each other at a distance of 32 amino acids apart, 62 amino acids apart, 28 amino acids apart, 1 amino acid apart, and 21 amino acids apart as arranged from the amino terminus to the carboxyl terminus of SEQ ID NO: 2.

18. The method of claim 17, wherein the agent that is administered binds to C5 but does not block the C5 convertase binding site.

19. The method of claim 17, wherein the agent that is administered has an amino acid sequence comprising or consisting of a sequence at least 95% identical to amino acids 19 to 168 of the amino acid sequence in SEQ ID NO: 2 or a sequence at least 95% identical to amino acids 1 to 168 of the amino acid sequence in SEQ ID NO: 2.

20. The method of claim 17, wherein the agent that is administered has an amino acid sequence comprising amino acids 19 to 168 or 1 to 168 of the amino acid sequence in SEQ ID NO: 2.

21. The method of claim 17, wherein the subject is a mammal.

22. The method of claim 17, wherein the subject is a human.

23. The method of claim 17, wherein the subject is a non-responder to anti-C5 monoclonal antibodies.

24. The method of claim 17, wherein the complement C5 polymorphism is Arg885Cys or Arg885His.

25. The method of claim 17, wherein the complement C5 polymorphism decreases the effectiveness of agents that inhibit, by blocking the C5 convertase binding site, the classical complement pathway, the alternative complement pathway and the lectin complement pathway.

26. The method of claim 17, wherein the subject with a complement C5 polymorphism is identified by:
   (a) a poor clinical response to an agent that inhibits at least one of the complement pathways; and/or
   (b) testing the ability of an agent that inhibits at least one of the complement pathways to inhibit complement activation in the subject; and/or
   (c) molecular genetic analysis.

27. The method of claim 17, wherein the subject with a complement C5 polymorphism is identified by a determination that a sample from the subject has at least 60% of normal serum complement activity in the presence of an anti-C5 monoclonal antibody, wherein the anti-C5 monoclonal antibody inhibits, in subjects with wild-type C5, the classical complement pathway, the alternative complement pathway, and the lectin complement pathway.

28. The method of claim 17, wherein the complement C5 polymorphism is identified or confirmed by sequencing the gene encoding C5 or other molecular genetic analysis.

29. A method of treating a complement-mediated disease and/or disorder comprising administering to a subject known to have an Arg885His complement C5 polymorphism and in need thereof a therapeutically effective amount of an agent that inhibits the classical complement pathway, the alternative complement pathway and the lectin complement pathway, wherein the agent is:
   i) a protein comprising an amino acid sequence having at least 90% sequence identity to amino acids 19 to 168 of SEQ ID NO: 2, or
   ii) a protein comprising an amino acid sequence having at least 90% sequence identity to amino acids 1 to 168 of SEQ ID NO: 2, or
   iii) a fragment of the complement inhibitor polypeptide of SEQ ID NO: 2, wherein said fragment comprises six cysteine residues that are spaced relative to each other at a distance of 32 amino acids apart, 62 amino acids apart, 28 amino acids apart, 1 amino acid apart, and 21 amino acids apart as arranged from the amino terminus to the carboxyl terminus of SEQ ID NO: 2;
   and wherein the complement C5 polymorphism decreases the effectiveness of one or more agents that inhibit, in a subject with wild-type C5, the classical complement pathway, the alternative complement pathway and the lectin complement pathway.

30. A method of treating a complement-mediated disease and/or disorder comprising administering to a subject known to have an Arg885Cys complement C5 polymorphism and in need thereof a therapeutically effective amount of an agent that inhibits the classical complement pathway, the alternative complement pathway and the lectin complement pathway, wherein the agent is:
   i) a protein comprising an amino acid sequence having at least 90% sequence identity to amino acids 19 to 168 of SEQ ID NO: 2, or
   ii) a protein comprising an amino acid sequence having at least 90% sequence identity to amino acids 1 to 168 of SEQ ID NO: 2, or
   iii) a fragment of the complement inhibitor polypeptide of SEQ ID NO: 2, wherein said fragment comprises six cysteine residues that are spaced relative to each other at a distance of 32 amino acids apart, 62 amino acids apart, 28 amino acids apart, 1 amino acid apart, and 21 amino acids apart as arranged from the amino terminus to the carboxyl terminus of SEQ ID NO: 2;
   and wherein the complement C5 polymorphism decreases the effectiveness of one or more agents that inhibit, in a subject with wild-type C5, the classical complement pathway, the alternative complement pathway and the lectin complement pathway.

\* \* \* \* \*

SEQUENCE LISTING

```
<160> NUMBER OF SEQ ID NOS: 14

<210> SEQ ID NO 1
<211> LENGTH: 507
<212> TYPE: DNA
<213> ORGANISM: Ornithodoros moubata

<400> SEQUENCE: 1
atgctggttt tggtgaccct gattttctcc ttttctgcga acatcgcata tgctgacagc      60
gaaagcgact gcactggaag cgaacctgtt gacgccttcc aagctttcag tgagggcaaa     120
gaggcatatg tcctggtgag gtccacggat cccaaagcga gggactgctt gaaaggagaa     180
ccagccggag aaaagcagga caacacgttg ccggtgatga tgacgtttaa gaatggcaca     240
gactgggctt caaccgattg gacgtttact ttggacggcg caaaggtaac ggcaaccctt     300
ggtaacctaa cccaaaatag ggaagtggtc tacgactcgc aaagtcatca ctgccacgtt     360
gacaaggtcg agaaggaagt tccagattat gagatgtgga tgctcgatgc gggagggctt     420
gaagtggaag tcgagtgctg ccgtcaaaag cttgaagagt tggcgtctgg caggaaccaa     480
atgtatcccc atctcaagga ctgctag                                         507

<210> SEQ ID NO 2
<211> LENGTH: 168
<212> TYPE: PRT
```

<213> ORGANISM: Ornithodoros moubata

<400> SEQUENCE: 2

Met Leu Val Leu Val Thr Leu Ile Phe Ser Phe Ser Ala Asn Ile Ala
1               5                   10                  15

Tyr Ala Asp Ser Glu Ser Asp Cys Thr Gly Ser Glu Pro Val Asp Ala
            20                  25                  30

Phe Gln Ala Phe Ser Glu Gly Lys Glu Ala Tyr Val Leu Val Arg Ser
        35                  40                  45

Thr Asp Pro Lys Ala Arg Asp Cys Leu Lys Gly Glu Pro Ala Gly Glu
    50                  55                  60

Lys Gln Asp Asn Thr Leu Pro Val Met Met Thr Phe Lys Asn Gly Thr
65                  70                  75                  80

Asp Trp Ala Ser Thr Asp Trp Thr Phe Thr Leu Asp Gly Ala Lys Val
                85                  90                  95

Thr Ala Thr Leu Gly Asn Leu Thr Gln Asn Arg Glu Val Val Tyr Asp
            100                 105                 110

Ser Gln Ser His His Cys His Val Asp Lys Val Glu Lys Glu Val Pro
        115                 120                 125

Asp Tyr Glu Met Trp Met Leu Asp Ala Gly Leu Glu Val Glu Val
    130                 135                 140

Glu Cys Cys Arg Gln Lys Leu Glu Gly Leu Ala Ser Gly Arg Asn Gln
145                 150                 155                 160

Met Tyr Pro His Leu Lys Asp Cys
                165

<210> SEQ ID NO 3
<211> LENGTH: 453
<212> TYPE: DNA
<213> ORGANISM: Ornithodoros moubata

<400> SEQUENCE: 3
gacagcgaaa gcgactgcac tggaagcgaa cctgttgacg ccttccaagc tttcagtgag      60
ggcaaagagg catatgtcct ggtgaggtcc acggatccca agcgaggga ctgcttgaaa      120 ggagaaccag ccggagaaaa gcaggacaac acgttgccgg tgatgatgac gtttaagaat      180
ggcacagact gggcttcaac cgattggacg tttactttgg acggcgcaaa ggtaacggca      240
acccttggta acctaaccca aaataggaa gtggtctacg actcgcaaag tcatcactgc      300
cacgttgaca aggtcgagaa ggaagttcca gattatgaga tgtggatgct cgatgcggga      360
gggcttgaag tggaagtcga gtgctgccgt caaaagcttg aagagttggc gtctggcagg      420
aaccaaatgt atccccatct caaggactgc tag                                   453

<210> SEQ ID NO 4
<211> LENGTH: 150
<212> TYPE: PRT
<213> ORGANISM: Ornithodoros moubata

<400> SEQUENCE: 4

Asp Ser Glu Ser Asp Cys Thr Gly Ser Glu Pro Val Asp Ala Phe Gln
1               5                   10                  15

Ala Phe Ser Glu Gly Lys Glu Ala Tyr Val Leu Val Arg Ser Thr Asp
            20                  25                  30

Pro Lys Ala Arg Asp Cys Leu Lys Gly Glu Pro Ala Gly Glu Lys Gln
        35                  40                  45

Asp Asn Thr Leu Pro Val Met Met Thr Phe Lys Asn Gly Thr Asp Trp

Ala Ser Thr Asp Trp Thr Phe Thr Leu Asp Gly Ala Lys Val Thr Ala
 65                  70                  75                  80

Thr Leu Gly Asn Leu Thr Gln Asn Arg Glu Val Val Tyr Asp Ser Gln
                 85                  90                  95

Ser His His Cys His Val Asp Lys Val Glu Lys Glu Val Pro Asp Tyr
            100                 105                 110

Glu Met Trp Met Leu Asp Ala Gly Gly Leu Glu Val Glu Val Glu Cys
        115                 120                 125

Cys Arg Gln Lys Leu Glu Glu Leu Ala Ser Gly Arg Asn Gln Met Tyr
    130                 135                 140

Pro His Leu Lys Asp Cys
145                 150

<210> SEQ ID NO 5
<211> LENGTH: 450
<212> TYPE: DNA
<213> ORGANISM: Ornithodoros moubata

<400> SEQUENCE: 5
agcgaaagcg actgcactgg aagcgaacct gttgacgcct tccaagcttt cagtgagggc      60
aaagaggcat atgtcctggt gaggtccacg gatcccaaag cgagggactg cttgaaagga     120
gaaccagccg gagaaaagca ggacaacacg ttgccggtga tgatgacgtt taagaatggc     180
acagactggg cttcaaccga ttggacgttt actttggacg gcgcaaaggt aacggcaacc     240
cttggtaacc taacccaaaa tagggaagtg gtctacgact cgcaaagtca tcactgccac     300
gttgacaagg tcgagaagga agttccagat tatgagatgt ggatgctcga tgcgggaggg     360
cttgaagtgg aagtcgagtg ctgccgtcaa aagcttgaag agttggcgtc tggcaggaac     420
caaatgtatc cccatctcaa ggactgctag                                      450

<210> SEQ ID NO 6
<211> LENGTH: 149
<212> TYPE: PRT
<213> ORGANISM: Ornithodoros moubata

<400> SEQUENCE: 6

Ser Glu Ser Asp Cys Thr Gly Ser Glu Pro Val Asp Ala Phe Gln Ala
  1               5                  10                  15

Phe Ser Glu Gly Lys Glu Ala Tyr Val Leu Val Arg Ser Thr Asp Pro
                 20                  25                  30

Lys Ala Arg Asp Cys Leu Lys Gly Glu Pro Ala Gly Glu Lys Gln Asp
             35                  40                  45

Asn Thr Leu Pro Val Met Met Thr Phe Lys Asn Gly Thr Asp Trp Ala
         50                  55                  60

Ser Thr Asp Trp Thr Phe Thr Leu Asp Gly Ala Lys Val Thr Ala Thr
 65                  70                  75                  80

Leu Gly Asn Leu Thr Gln Asn Arg Glu Val Val Tyr Asp Ser Gln Ser
                 85                  90                  95

His His Cys His Val Asp Lys Val Glu Lys Glu Val Pro Asp Tyr Glu
            100                 105                 110

Met Trp Met Leu Asp Ala Gly Gly Leu Glu Val Glu Val Glu Cys Cys
        115                 120                 125

Arg Gln Lys Leu Glu Glu Leu Ala Ser Gly Arg Asn Gln Met Tyr Pro
    130                 135                 140

```
His Leu Lys Asp Cys
145

<210> SEQ ID NO 7
<211> LENGTH: 447
<212> TYPE: DNA
<213> ORGANISM: Ornithodoros moubata

<400> SEQUENCE: 7
gaaagcgact gcactggaag cgaacctgtt gacgccttcc aagctttcag tgagggcaaa      60
gaggcatatg tcctggtgag gtccacggat cccaaagcga gggactgctt gaaaggagaa     120
ccagccggag aaaagcagga caacacgttg ccggtgatga tgacgtttaa gaatggcaca     180
gactgggctt caaccgattg gacgtttact ttggacggcg caaaggtaac ggcaacccct     240
ggtaacctaa cccaaaatag ggaagtggtc tacgactcgc aaagtcatca ctgccacgtt     300
gacaaggtcg agaaggaagt tccagattat gagatgtgga tgctcgatgc gggagggctt     360
gaagtggaag tcgagtgctg ccgtcaaaag cttgaagagt tggcgtctgg caggaaccaa     420
atgtatcccc atctcaagga ctgctag                                        447

<210> SEQ ID NO 8
<211> LENGTH: 148
<212> TYPE: PRT
<213> ORGANISM: Ornithodoros moubata

<400> SEQUENCE: 8

Glu Ser Asp Cys Thr Gly Ser Glu Pro Val Asp Ala Phe Gln Ala Phe
1               5                   10                  15

Ser Glu Gly Lys Glu Ala Tyr Val Leu Val Arg Ser Thr Asp Pro Lys
            20                  25                  30

Ala Arg Asp Cys Leu Lys Gly Glu Pro Ala Gly Glu Lys Gln Asp Asn
        35                  40                  45

Thr Leu Pro Val Met Met Thr Phe Lys Asn Gly Thr Asp Trp Ala Ser
    50                  55                  60

Thr Asp Trp Thr Phe Thr Leu Asp Gly Ala Lys Val Thr Ala Thr Leu
65                  70                  75                  80

Gly Asn Leu Thr Gln Asn Arg Glu Val Val Tyr Asp Ser Gln Ser His
                85                  90                  95

His Cys His Val Asp Lys Val Glu Lys Glu Val Pro Asp Tyr Glu Met
            100                 105                 110

Trp Met Leu Asp Ala Gly Gly Leu Glu Val Glu Val Glu Cys Cys Arg
        115                 120                 125

Gln Lys Leu Glu Glu Leu Ala Ser Gly Arg Asn Gln Met Tyr Pro His
    130                 135                 140

Leu Lys Asp Cys
145

<210> SEQ ID NO 9
<211> LENGTH: 444
<212> TYPE: DNA
<213> ORGANISM: Ornithodoros moubata

<400> SEQUENCE: 9
agcgactgca ctggaagcga acctgttgac gccttccaag ctttcagtga gggcaaagag      60
gcatatgtcc tggtgaggtc cacggatccc aaagcgaggg actgcttgaa aggagaacca     120
gccggagaaa agcaggacaa cacgttgccg gtgatgatga cgtttaagaa tggcacagac     180
```

```
tgggcttcaa ccgattggac gtttactttg gacggcgcaa aggtaacggc aaccccttggt      240 aacctaaccc aaaataggga agtggtctac gactcgcaaa gtcatcactg ccacgttgac      300
aaggtcgaga aggaagttcc agattatgag atgtggatgc tcgatgcggg agggcttgaa      360
gtggaagtcg agtgctgccg tcaaaagctt gaagagttgg cgtctggcag gaaccaaatg      420
tatccccatc tcaaggactg ctag                                             444
```

<210> SEQ ID NO 10
<211> LENGTH: 147
<212> TYPE: PRT
<213> ORGANISM: Ornithodoros moubata

<400> SEQUENCE: 10

```
Ser Asp Cys Thr Gly Ser Glu Pro Val Asp Ala Phe Gln Ala Phe Ser
1               5                   10                  15

Glu Gly Lys Glu Ala Tyr Val Leu Val Arg Ser Thr Asp Pro Lys Ala
            20                  25                  30

Arg Asp Cys Leu Lys Gly Glu Pro Ala Gly Glu Lys Gln Asp Asn Thr
        35                  40                  45

Leu Pro Val Met Met Thr Phe Lys Asn Gly Thr Asp Trp Ala Ser Thr
    50                  55                  60

Asp Trp Thr Phe Thr Leu Asp Gly Ala Lys Val Thr Ala Thr Leu Gly
65                  70                  75                  80

Asn Leu Thr Gln Asn Arg Glu Val Val Tyr Asp Ser Gln Ser His His
                85                  90                  95

Cys His Val Asp Lys Val Glu Lys Glu Val Pro Asp Tyr Glu Met Trp
            100                 105                 110

Met Leu Asp Ala Gly Gly Leu Glu Val Glu Val Glu Cys Cys Arg Gln
        115                 120                 125

Lys Leu Glu Glu Leu Ala Ser Gly Arg Asn Gln Met Tyr Pro His Leu
    130                 135                 140

Lys Asp Cys
145
```

<210> SEQ ID NO 11
<211> LENGTH: 441
<212> TYPE: DNA
<213> ORGANISM: Ornithodoros moubata

<400> SEQUENCE: 11

```
gactgcactg gaagcgaacc tgttgacgcc ttccaagctt tcagtgaggg caaagaggca       60
tatgtcctgg tgaggtccac ggatcccaaa gcgagggact gcttgaaagg agaaccagcc     120
ggagaaaagc aggacaacac gttgccggtg atgatgacgt taagaatgg cacagactgg      180 gcttcaaccg attggacgtt tactttggac ggcgcaaagg taacggcaac ccttggtaac    240
ctaacccaaa atagggaagt ggtctacgac tcgcaaagtc atcactgcca cgttgacaag    300
gtcgagaagg aagttccaga ttatgagatg tggatgctcg atgcgggagg gcttgaagtg    360
gaagtcgagt gctgccgtca aaagcttgaa gagttggcgt ctggcaggaa ccaaatgtat    420
ccccatctca aggactgcta g                                               441
```

<210> SEQ ID NO 12
<211> LENGTH: 146
<212> TYPE: PRT
<213> ORGANISM: Ornithodoros moubata

<400> SEQUENCE: 12

```
Asp Cys Thr Gly Ser Glu Pro Val Asp Ala Phe Gln Ala Phe Ser Glu
1               5                   10                  15

Gly Lys Glu Ala Tyr Val Leu Val Arg Ser Thr Asp Pro Lys Ala Arg
            20                  25                  30

Asp Cys Leu Lys Gly Glu Pro Ala Gly Glu Lys Gln Asp Asn Thr Leu
        35                  40                  45

Pro Val Met Met Thr Phe Lys Asn Gly Thr Asp Trp Ala Ser Thr Asp
    50                  55                  60

Trp Thr Phe Thr Leu Asp Gly Ala Lys Val Thr Ala Thr Leu Gly Asn
65              70                  75                  80

Leu Thr Gln Asn Arg Glu Val Val Tyr Asp Ser Gln Ser His His Cys
                85                  90                  95

His Val Asp Lys Val Glu Lys Glu Val Pro Tyr Glu Met Trp Met
            100                 105                 110

Leu Asp Ala Gly Gly Leu Glu Val Val Glu Cys Cys Arg Gln Lys
        115                 120                 125

Leu Glu Glu Leu Ala Ser Gly Arg Asn Gln Met Tyr Pro His Leu Lys
    130                 135                 140

Asp Cys
145
```

```
<210> SEQ ID NO 13
<211> LENGTH: 438
<212> TYPE: DNA
<213> ORGANISM: Ornithodoros moubata

<400> SEQUENCE: 13
tgcactggaa gcgaacctgt tgacgccttc caagctttca gtgagggcaa agaggcatat      60
gtcctggtga ggtccacgga tcccaaagcg agggactgct tgaaaggaga ccagccgga     120
gaaaagcagg acaacacgtt gccggtgatg atgacgttta agaatggcac agactgggct     180
tcaaccgatt ggacgtttac tttggacggc gcaaaggtaa cggcaaccct tggtaaccta     240
acccaaaata gggaagtggt ctacgactcg caaagtcatc actgccacgt tgacaaggtc     300
gagaaggaag ttccagatta tgagatgtgg atgctcgatg cggagggct tgaagtggaa      360
gtcgagtgct gccgtcaaaa gcttgaagag ttggcgtctg gcaggaacca aatgtatccc    420
catctcaagg actgctag                                                   438
```

```
<210> SEQ ID NO 14
<211> LENGTH: 145
<212> TYPE: PRT
<213> ORGANISM: Ornithodoros moubata

<400> SEQUENCE: 14

Cys Thr Gly Ser Glu Pro Val Asp Ala Phe Gln Ala Phe Ser Glu Gly
1               5                   10                  15

Lys Glu Ala Tyr Val Leu Val Arg Ser Thr Asp Pro Lys Ala Arg Asp
            20                  25                  30

Cys Leu Lys Gly Glu Pro Ala Gly Glu Lys Gln Asp Asn Thr Leu Pro
        35                  40                  45

Val Met Met Thr Phe Lys Asn Gly Thr Asp Trp Ala Ser Thr Asp Trp
    50                  55                  60

Thr Phe Thr Leu Asp Gly Ala Lys Val Thr Ala Thr Leu Gly Asn Leu
65              70                  75                  80

Thr Gln Asn Arg Glu Val Val Tyr Asp Ser Gln Ser His His Cys His
```

-continued

```
                85                  90                  95
Val Asp Lys Val Glu Lys Glu Val Pro Asp Tyr Glu Met Trp Met Leu
            100                 105                 110

Asp Ala Gly Gly Leu Glu Val Glu Val Glu Cys Cys Arg Gln Lys Leu
            115                 120                 125

Glu Glu Leu Ala Ser Gly Arg Asn Gln Met Tyr Pro His Leu Lys Asp
            130                 135                 140

Cys
145
```

UNITED STATES PATENT AND TRADEMARK OFFICE
CERTIFICATE OF CORRECTION

| | | |
|---|---|---|
| PATENT NO. | : 11,052,129 B2 | Page 1 of 1 |
| APPLICATION NO. | : 15/315136 | |
| DATED | : July 6, 2021 | |
| INVENTOR(S) | : Weston-Davies | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 469 days.

Signed and Sealed this
Twentieth Day of December, 2022

*Katherine Kelly Vidal*

Katherine Kelly Vidal
*Director of the United States Patent and Trademark Office*